(12) United States Patent
Wagner et al.

(10) Patent No.: US 7,392,081 B2
(45) Date of Patent: Jun. 24, 2008

(54) SUBCUTANEOUS CARDIAC STIMULATOR EMPLOYING POST-SHOCK TRANSTHORACIC ASYSTOLE PREVENTION PACING

(75) Inventors: Darrell Orvin Wagner, Isanti, MN (US); Adam W. Cates, Minneapolis, MN (US); Kristine M. Larsen-Kelly, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 790 days.

(21) Appl. No.: 10/377,274

(22) Filed: Feb. 28, 2003

(65) Prior Publication Data

US 2004/0172066 A1 Sep. 2, 2004

(51) Int. Cl.
*A61N 1/00* (2006.01)
(52) U.S. Cl. .......................................................... 607/4
(58) Field of Classification Search ................. 607/4–9; 600/515
See application file for complete search history.

(56) References Cited

U.S. PATENT DOCUMENTS

| | | | |
|---|---|---|---|
| 4,562,841 A | 1/1986 | Brockway et al. | |
| 4,693,253 A * | 9/1987 | Adams | 607/4 |
| 4,940,054 A * | 7/1990 | Grevis et al. | 607/4 |
| 4,953,551 A | 9/1990 | Mehra et al. | |
| 5,036,849 A | 8/1991 | Hauck et al. | |
| 5,133,353 A | 7/1992 | Hauser | |
| 5,170,784 A | 12/1992 | Ramon et al. | |
| 5,179,945 A | 1/1993 | Van Hofwegen et al. | |
| 5,203,348 A | 4/1993 | Dahl et al. | |
| 5,209,229 A | 5/1993 | Gilli | |
| 5,230,337 A | 7/1993 | Dahl et al. | |
| 5,261,400 A | 11/1993 | Bardy | |
| 5,284,136 A | 2/1994 | Hauck et al. | |
| 5,292,338 A | 3/1994 | Bardy | |
| 5,300,106 A | 4/1994 | Dahl et al. | |
| 5,301,677 A | 4/1994 | Hsung | |
| 5,306,293 A | 4/1994 | Zacouto | |
| 5,313,953 A | 5/1994 | Yomtov et al. | |
| 5,314,430 A | 5/1994 | Bardy | |
| 5,314,459 A | 5/1994 | Swanson et al. | |
| 5,331,966 A | 7/1994 | Bennett et al. | |

(Continued)

FOREIGN PATENT DOCUMENTS

WO WO 92/20402 11/1992

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—Scott M Getzow
(74) *Attorney, Agent, or Firm*—Hollingsworth & Funk, LLC

(57) ABSTRACT

Transthoracic cardiac stimulation therapies provide for detection and treatment of cardiac asystole subsequent to delivery of a defibrillation therapy. A pacing therapy is transthoracicly delivered to terminate detected cardiac asystole using residual energy from a defibrillation energy storage source. The residual energy usable for the pacing therapy is sufficient to transthoracicly deliver at least one pacing pulse, and is typically sufficient to deliver a series of pacing pulses, prior to depletion of the defibrillation energy storage source. Detection of cardiac asystole is performed following delivery of each pacing pulse, and subcutaneous pacing support is terminated in response to detecting cardiac asystole termination.

83 Claims, 12 Drawing Sheets

U.S. PATENT DOCUMENTS

| | | | |
|---|---|---|---|
| 5,360,442 A | 11/1994 | Dahl et al. | |
| 5,366,496 A | 11/1994 | Dahl et al. | |
| 5,372,606 A | 12/1994 | Lang et al. | |
| 5,376,106 A | 12/1994 | Stahmann et al. | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,525 A | 5/1995 | Swanson et al. | |
| 5,411,539 A | 5/1995 | Neisz | |
| 5,439,482 A | 8/1995 | Adams et al. | |
| 5,441,518 A | 8/1995 | Adams et al. | |
| 5,468,254 A | 11/1995 | Hahn et al. | |
| 5,531,779 A | 7/1996 | Dahl et al. | |
| 5,545,202 A | 8/1996 | Dahl et al. | |
| 5,603,732 A | 2/1997 | Dahl et al. | |
| 5,620,466 A | 4/1997 | Haefner et al. | |
| 5,634,938 A | 6/1997 | Swanson et al. | |
| 5,641,326 A | 6/1997 | Adams | |
| 5,662,688 A | 9/1997 | Haefner et al. | |
| 5,697,953 A | 12/1997 | Kroll et al. | |
| 5,704,365 A | 1/1998 | Albrecht et al. | |
| 5,724,984 A | 3/1998 | Arnold et al. | |
| 5,797,967 A * | 8/1998 | KenKnight | 607/4 |
| 5,827,326 A | 10/1998 | Kroll et al. | |
| 5,895,414 A | 4/1999 | Sanchez-Zambrano | |
| 5,916,243 A | 6/1999 | KenKnight et al. | |
| 5,957,956 A | 9/1999 | Kroll et al. | |
| 6,044,298 A | 3/2000 | Salo et al. | |
| 6,055,454 A | 4/2000 | Heemels | |
| 6,148,230 A | 11/2000 | KenKnight | |
| 6,280,462 B1 | 8/2001 | Hauser et al. | |
| 6,304,773 B1 * | 10/2001 | Taylor et al. | 600/515 |
| 6,438,410 B2 | 8/2002 | Hsu et al. | |
| 6,512,940 B1 | 1/2003 | Brabec et al. | |
| 6,522,915 B1 | 2/2003 | Ceballos et al. | |
| 6,564,106 B2 | 5/2003 | Guck et al. | |
| 6,607,509 B2 | 8/2003 | Bobroff et al. | |
| 6,615,083 B2 | 9/2003 | Kupper | |
| 6,622,046 B2 | 9/2003 | Fraley et al. | |
| 2002/0035376 A1 | 3/2002 | Bardy et al. | |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035380 A1 | 3/2002 | Rissmann et al. | |
| 2002/0035381 A1 | 3/2002 | Bardy et al. | |
| 2002/0042629 A1 | 4/2002 | Bardy et al. | |
| 2002/0042630 A1 | 4/2002 | Bardy et al. | |
| 2002/0042634 A1 | 4/2002 | Bardy et al. | |
| 2002/0049475 A1 | 4/2002 | Bardy et al. | |
| 2002/0049476 A1 | 4/2002 | Bardy et al. | |
| 2002/0052636 A1 | 5/2002 | Bardy et al. | |
| 2002/0068958 A1 | 6/2002 | Bardy et al. | |
| 2002/0072773 A1 | 6/2002 | Bardy et al. | |
| 2002/0082658 A1 | 6/2002 | Heinrich et al. | |
| 2002/0091414 A1 | 7/2002 | Bardy et al. | |
| 2002/0095184 A1 | 7/2002 | Bardy et al. | |
| 2002/0103510 A1 | 8/2002 | Bardy et al. | |
| 2002/0107544 A1 | 8/2002 | Ostroff et al. | |
| 2002/0107545 A1 | 8/2002 | Rissmann et al. | |
| 2002/0107546 A1 | 8/2002 | Ostroff et al. | |
| 2002/0107547 A1 | 8/2002 | Erlinger et al. | |
| 2002/0107548 A1 | 8/2002 | Bardy et al. | |
| 2002/0107549 A1 | 8/2002 | Bardy et al. | |
| 2002/0107553 A1 | 8/2002 | Hill et al. | |
| 2002/0107559 A1 | 8/2002 | Sanders et al. | |
| 2002/0120299 A1 | 8/2002 | Ostroff et al. | |
| 2003/0004546 A1 | 1/2003 | Casey | |
| 2003/0004552 A1 | 1/2003 | Plombon et al. | |
| 2003/0023175 A1 | 1/2003 | Arzbaecher et al. | |
| 2003/0036778 A1 | 2/2003 | Ostroff et al. | |
| 2003/0045904 A1 | 3/2003 | Bardy et al. | |
| 2003/0069609 A1 | 4/2003 | Thompson | |
| 2003/0088278 A1 | 5/2003 | Bardy et al. | |
| 2003/0088279 A1 | 5/2003 | Rissmann et al. | |
| 2003/0088280 A1 | 5/2003 | Ostroff | |
| 2003/0088281 A1 | 5/2003 | Ostroff et al. | |
| 2003/0088282 A1 | 5/2003 | Ostroff | |
| 2003/0088283 A1 | 5/2003 | Ostroff | |
| 2003/0088286 A1 | 5/2003 | Ostroff et al. | |
| 2003/0097153 A1 | 5/2003 | Bardy et al. | |
| 2003/0114887 A1 | 6/2003 | Keknight | |
| 2003/0163169 A1 | 8/2003 | Hill et al. | |
| 2003/0204216 A1 | 10/2003 | Ries et al. | |
| 2003/0212436 A1 | 11/2003 | Brown | |
| 2004/0064177 A1 | 4/2004 | Bardy et al. | |

OTHER PUBLICATIONS

Theofilos M. Kolettis, MD, PhD et al., *Submemmary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*, Europace Supplements, vol. 2, Jun. 2001 at B83.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter in Children*, J. of Cardiovascular Electrophysiology, vol. 12, No. 3, pp. 356-360 (Mar. 2001).

Giuliano Altamura et al., *Emergency Cardiac Pacing for Severe Bradycardia*, PACE, vol. 13, pp. 2038-2043 (Dec. 1990) Part II.

*Noninvasive Pacing Application Note*, Agilent Technologies, Inc., pp. 1-12 (Jan. 2000).

* cited by examiner

Shock    Pacing at 70 ppm

SUBCUTANEOUS CARDIAC STIMULATOR EMPLOYING POST-SHOCK TRANSTHORACIC ASYSTOLE PREVENTION PACING

FIELD OF THE INVENTION

The present invention relates generally to implantable medical devices and, more particularly, to cardiac stimulation methods and systems that provide transthoracic defibrillation and pacing therapies, including pacing therapies directed to terminating post-shock cardiac asystole.

BACKGROUND OF THE INVENTION

The healthy heart produces regular, synchronized contractions. Rhythmic contractions of the heart are normally controlled by the sinoatrial (SA) node, which are specialized cells located in the upper right atrium. The SA node is the normal pacemaker of the heart, typically initiating 60-100 heart beats per minute. When the SA node is pacing the heart normally, the heart is said to be in normal sinus rhythm.

If heart contractions are uncoordinated or irregular, the heart is denoted to be arrhythmic. Cardiac arrhythmia impairs cardiac efficiency and can be a potential life threatening event. Cardiac arrythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid, uncoordinated contractions of the atria. Besides being hemodynamically inefficient, the rapid contractions of the atria can also adversely affect the ventricular rate. This occurs when the aberrant contractile impulses in the atria are transmitted to the ventricles. It is then possible for the aberrant atrial signals to induce ventricular tachyarrhythmias.

Ventricular tachycardia occurs, for example, when electrical activity arises in the ventricular myocardium at a rate more rapid than the normal sinus rhythm. Ventricular tachycardia can quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses which are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating the arrythmias described above.

Implantable cardioverter/defibrillators (ICDs) have been used as an effective treatment for patients with serious cardiac arrhythmias. For example, a typical ICD includes one or more endocardial leads to which at least one defibrillation electrode is connected. Such ICDs are capable of delivering high energy shocks to the heart, interrupting the ventricular tachyarrythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. The primary reasons for this unfortunate reality include the limited number of physicians qualified to perform transvenous lead/electrode implantation, a limited number of surgical facilities adequately equipped to accommodate such cardiac procedures, and a limited number of the at-risk patient population that can safely undergo the required endocardial or epicardial lead/electrode implant procedure.

For reasons stated above, and for other reasons which will become apparent to those skilled in the art upon reading the present specification, there is a need for systems and methods that provide for sensing cardiac activity without the need for endocardial or epicardial leads/electrodes. There is a further need for systems and methods that provide for delivering cardiac stimulation therapy without the need for endocardial or epicardial leads/electrodes. There is yet a further need for detecting and treating post-shock cardiac asystole by such systems and methods. The present invention fulfills these and other needs, and addresses deficiencies in known systems and techniques.

SUMMARY OF THE INVENTION

The present invention is directed to cardiac stimulation methods and systems that, in general, provide transthoracic defibrillation therapies, transthoracic pacing therapies, or a combination of transthoracic defibrillation and pacing therapies. Embodiments of the present invention include those directed to subcutaneous cardiac stimulation methods and systems that detect and treat cardiac asystole that arises subsequent to delivery of a defibrillation therapy.

According to one embodiment, a method of providing subcutaneous cardiac stimulation involves detecting cardiac asystole subsequent to delivery of a defibrillation therapy, wherein energy for the defibrillation therapy is provided by a subcutaneous defibrillation energy storage source. The method further involves transthoracicly delivering a pacing therapy to terminate the detected cardiac asystole using residual energy from the defibrillation energy storage source. The residual energy usable for the pacing therapy is sufficient to transthoracicly deliver at least one pacing pulse, and is typically sufficient to deliver a series of pacing pulses prior to depletion of the defibrillation energy storage source. Detection of cardiac asystole is performed following delivery of each pacing pulse, and subcutaneous pacing support is terminated in response to detecting cardiac asystole termination.

According to another embodiment, a method of providing subcutaneous pacing support involves detecting cardiac asystole subsequent to delivery of a defibrillation therapy, and transthoracicly delivering a non-physiologic, life sustaining pacing therapy to terminate the detected cardiac asystole. Delivering the pacing therapy according to this embodiment involves delivering pacing pulses at a rate substantially lower than a bradycardia pacing rate. For example, pacing pulses are typically delivered at a rate varying between about 2 and about 40 pulses per minute. The pacing therapy can involve delivering a first pace pulse about 5 to 30 seconds subsequent to detection of the cardiac asystole. Pacing pulses can be delivered at a progressively increasing rate or at a substantially constant rate. Delivering the pacing therapy can involve delivering a series of pacing pulses, wherein the series of pacing pulses includes at least one sequence delivered at a variable rate and at least one sequence delivered at a substantially constant rate.

In accordance with another embodiment, a method of providing subcutaneous pacing support involves detecting cardiac asystole subsequent to delivery of a defibrillation therapy, and transthoracicly delivering a life sustaining pacing therapy at a rate insufficient to restore full patient consciousness to terminate the detected cardiac asystole. Delivering the pacing therapy involves delivering pacing pulses at a rate substantially lower than a bradycardia pacing rate.

According to a further embodiment, a method of providing cardiac stimulation involves delivering a cardioversion or defibrillation therapy in response to detecting a cardiac arrhythmia necessitating cardioversion or defibrillation therapy. Energy for the cardioversion or defibrillation therapy is provided by a subcutaneous cardioversion/defibrillation energy storage source. The method further involves transthoracicly delivering a pacing therapy in response to detecting a condition necessitating pacing therapy, wherein energy for the pacing therapy delivery is provided by the defibrillation energy storage source. The condition necessitating pacing therapy can be a bradycardia condition or a tachycardia condition.

In accordance with another embodiment of the present invention, an apparatus for providing subcutaneous cardiac stimulation includes a housing and energy delivery circuitry provided in the housing. The energy delivery circuitry includes a defibrillation energy storage source. First and second electrodes are respectively coupled to the energy delivery circuitry and are arranged in a spaced relationship with respect to cardiac tissue and vasculature for transthoracic cardiac sensing and energy delivery. Detection/control circuitry is provided in the housing and coupled to the energy delivery circuitry. The detection/control circuitry detects cardiac asystole subsequent to delivery of a defibrillation therapy, and initiates a transthoracic pacing therapy via the energy delivery circuitry to terminate the detected cardiac asystole using residual energy from the defibrillation energy storage source.

In one configuration, the first electrode is provided on the housing, and the second electrode is electrically and physically coupled to the housing via a lead. In another configuration, the housing defines a unitary structure, and each of the first and second electrodes is provided on the housing. The unitary housing can include an arcuate or angled portion, and the first and second electrodes are respectively positioned proximate opposing ends of the unitary housing.

In another configuration, one of the first and second electrodes is provided on the housing, and the other of the first and second electrodes is provided on a support structure outwardly extending from the housing. All or a portion of the support structure can include a shape adjustable arrangement, whereby an orientation between the first and second electrodes is alterable in response to manual manipulation of the shape adjustable arrangement.

In yet another configuration, the first electrode is provided on the housing and the second electrode is provided on a support structure extending outwardly from the housing. The support structure includes an arcuate or angled portion relative to the housing, and the second electrode is positioned distal to an inflection point of the arcuate or angled portion. A header block or other type of coupler is disposed between the housing and the support structure for establishing electrical connections between electrode conductors and corresponding electrical terminals in the housing.

According to another embodiment, an apparatus for providing subcutaneous pacing support includes a housing and energy delivery circuitry provided in the housing. First and second electrodes are respectively coupled to the energy delivery circuitry and are arranged in a spaced relationship with respect to cardiac tissue and vasculature for transthoracic cardiac sensing and energy delivery. Detection/control circuitry is provided in the housing and coupled to the energy delivery circuitry. The detection/control circuitry detects cardiac asystole subsequent to delivery of a defibrillation therapy, and initiates a transthoracic, non-physiologic life sustaining pacing therapy via the energy delivery circuitry to terminate the detected cardiac asystole.

The defibrillation therapy and the pacing therapy, in one configuration, derive energy from a defibrillation energy storage source of the energy delivery circuitry. In another configuration, separate pacing circuitry is coupled to the detection/control circuitry, wherein the energy delivery circuitry delivers the defibrillation therapy and the pacing circuitry delivers the pacing therapy.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
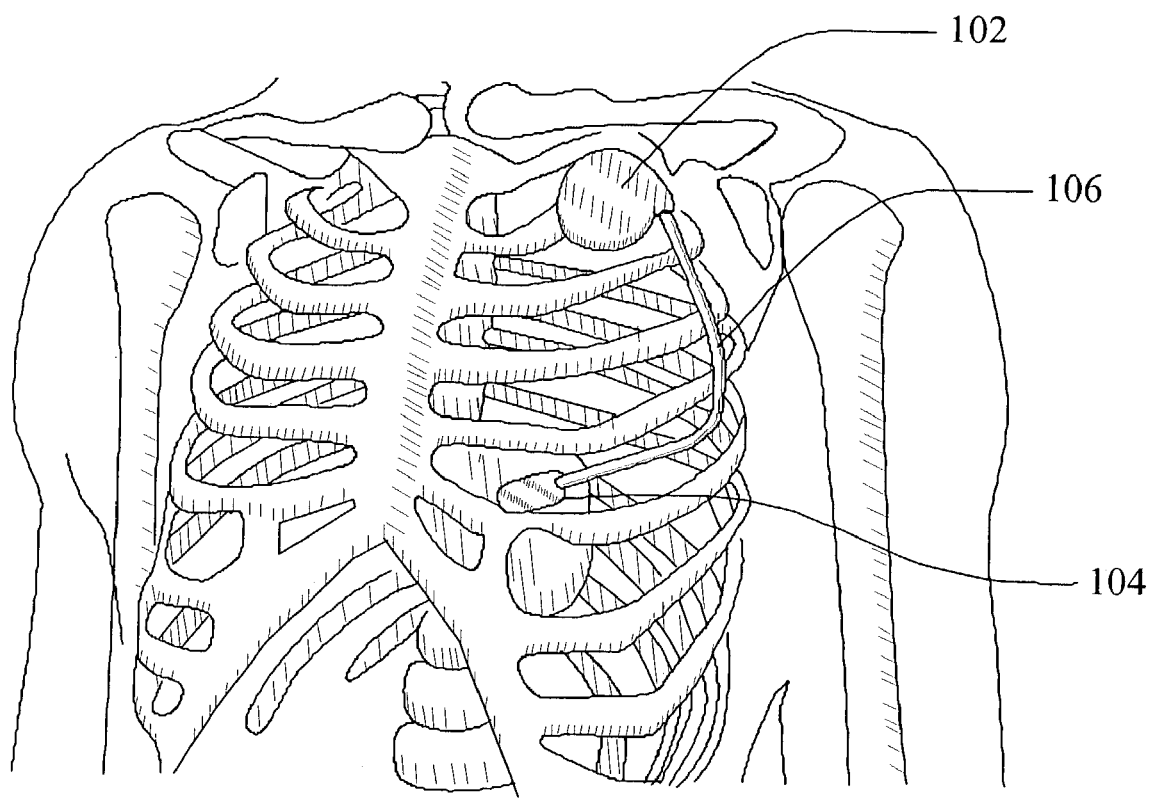
FIGS. 1A and 1B are views of a transthoracic cardiac stimulation device as implanted in a patient in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In general terms, an implantable transthoracic cardiac stimulation (ITCS) device of the present invention can be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions of the heart. The primary housing (e.g., the active or non-active can) of the ITCS, for example, can be configured for positioning outside of the rib cage at an intercostal or subcostal location, within the abdomen, or in the upper chest region (e.g., subclavian location, such as above the third rib). One or more electrodes can be located on the primary housing and/or at other locations about, but not in direct contact with, the heart or cardiac vessels. One or more subcutaneous electrode arrays, for example, can be used to sense cardiac activity and deliver cardiac stimulation energy in an ITCS configuration employing an active can or a configuration employing a non-active can.

Certain embodiments of the present invention illustrated herein are generally described as capable of implementing various functions traditionally performed by an implantable cardioverter/defibrillator (ICD), and may operate in numerous cardioversion/defibrillation modes as are known in the art. Exemplary ICD circuitry, structures and functionality, aspects of which can be incorporated in an ITCS device of the present invention, are disclosed in commonly owned U.S. Pat. Nos. 5,133,353; 5,179,945; 5,314,459; 5,620,466; and 5,662,688, which are hereby incorporated herein by reference in their respective entireties.

In particular embodiments, the systems and methods of the present invention can perform functions traditionally performed by pacemakers, such as providing various pacing therapies as are known in the art, in addition to cardioversion/defibrillation therapies. Exemplary pacemaker circuitry, structures and functionality, aspects of which can be incorporated in an ITCS device of the present invention, are disclosed in commonly owned U.S. Pat. Nos. 4,562,841; 5,284,136; 5,376,106; 5,036,849; 6,044,298; and 6,055,454, which are hereby incorporated herein by reference in their respective entireties. Systems and methods of the present invention can provide for non-physiologic pacing support in addition to, or to the exclusion of, bradycardia and/or anti-tachycardia pacing therapies.

Systems and methods of the present invention can implement functionality traditionally provided by cardiac monitors as are known in the art, in addition to providing cardioversion/defibrillation therapies. Exemplary cardiac monitoring circuitry, structures and functionality, aspects of which can be incorporated in an ITCS device of the present invention, are disclosed in commonly owned U.S. Pat. Nos. 5,313,953; 5,388,578; and 5,411,031, which are hereby incorporated herein by reference in their respective entireties.

Devices of the present invention may implement various anti-tachyarrhythmia therapies, such as tiered therapies, which may involve performing rate-based and/or morphological tachyarrhythmia discrimination analyses. Subcutaneous, cutaneous, and/or external sensors can be employed to acquire physiologic and non-physiologic information for purposes of enhancing tachyarrhythmia detection and termination. It is understood that embodiments and features of the present invention can be implemented in a wide range of implantable medical devices, and that such embodiments and features are not limited to the particular devices described herein.

Figure 1B:
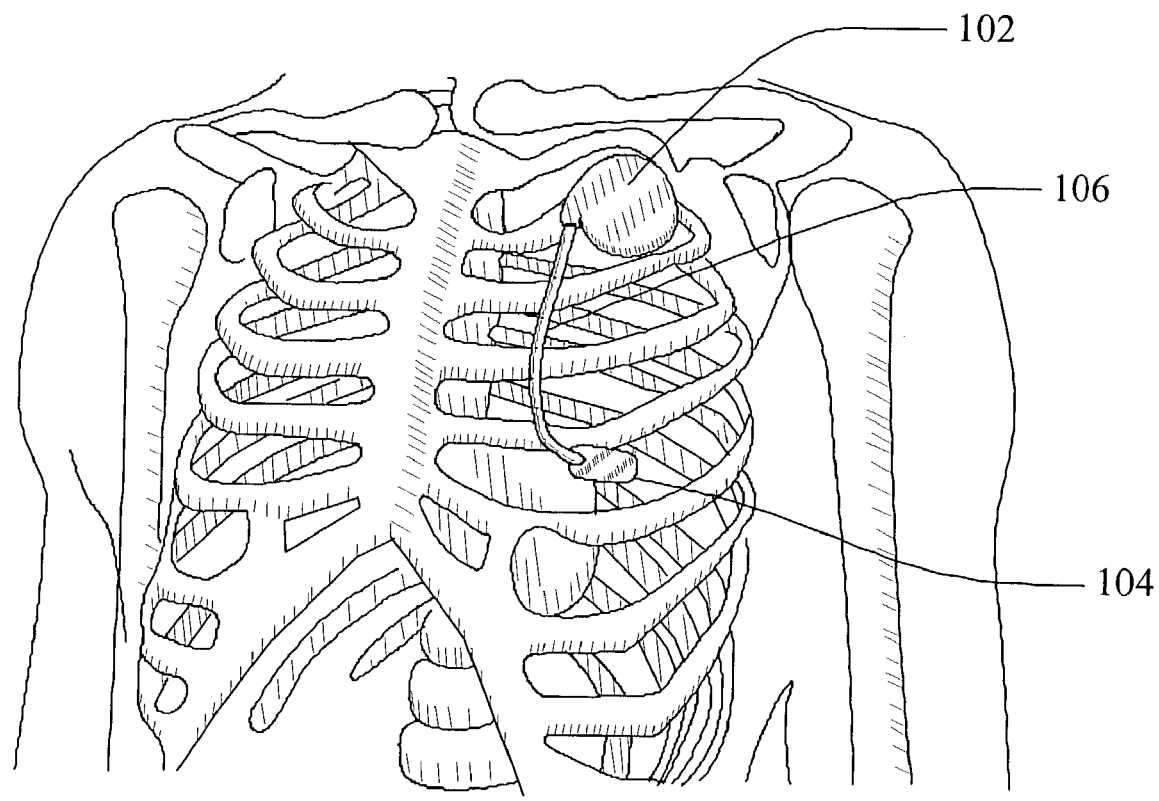

Referring now to FIGS. 1A and 1B of the drawings, there is shown one embodiment of a transthoracic cardiac stimulation (ITCS) device implanted in the chest region of a patient at different locations. In the particular embodiment shown in FIGS. 1A and 1B, the ITCS device includes a housing 102 within which various cardiac sensing, detection, processing, and energy delivery circuitry can be housed. It is understood that the components and functionality depicted in the figures and described herein can be implemented in hardware, software, or a combination of hardware and software. It is further understood that the components and functionality depicted as separate or discrete blocks/elements in the figures can be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 1A and 1B, a subcutaneous electrode 104 can be positioned under the skin in the chest region and situated distal from the housing 102. The subcutaneous electrode 104 is electrically coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes can be situated on the elongated structure of the electrode support, the housing 102, and/or the distal electrode assembly (shown as subcutaneous electrode 104 in the embodiment shown in FIGS. 1A and 1B).

In one embodiment, the lead assembly 106 is generally flexible and has a construction similar to conventional body implantable, medical electrical leads (e.g., defibrillation leads or combined defibrillation/pacing leads). In another embodiment, the lead assembly 106 is constructed to be somewhat flexible, yet has an elastic, spring, or mechanical memory that retains a desired configuration after being shaped or manipulated by a clinician. For example, the lead assembly 106 can incorporate a gooseneck or braid system that can be distorted under manual force to take on a desired shape. In this manner, the lead assembly 106 can be shape-fit to accommodate the unique anatomical configuration of a given patient, and generally retains a customized shape after implantation. Shaping of the lead assembly 106 according to this configuration can occur prior to, and during, ITCS implantation.

In accordance with a further embodiment, the lead assembly 106 includes a rigid electrode support assembly, such as a rigid elongated structure that positionally stabilizes the subcutaneous electrode 104 with respect to the housing 102. In this embodiment, the rigidity of the elongated structure maintains a desired spacing between the subcutaneous electrode 104 and the housing 102, and a desired orientation of the subcutaneous electrode 104/housing 102 relative to the patient's heart. The elongated structure can be formed from a structural plastic, composite or metallic material, and comprises, or is covered by, a biocompatible material. Appropriate electrical isolation between the housing 102 and subcutaneous electrode 104 is provided in cases where the elongated structure is formed from an electrically conductive material, such as metal.

In one configuration, the rigid electrode support assembly and the housing 102 define a unitary structure (i.e., a single housing/unit). The electronic components and electrode conductors/connectors are disposed within or on the unitary ITCS housing/electrode support assembly. At least two electrodes are supported on the unitary structure near opposing ends of the housing/electrode support assembly. The unitary structure can have an arcuate or angled shape, for example.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement can be configured to include both electrical and mechanical couplings that provide for mechanical and electrical connections between the rigid electrode support assembly and housing 102. The header block arrangement can be provided on the housing 102 or the rigid electrode support assembly. Alternatively, a mechanical/electrical coupler can be used to establish mechanical and electrical connections between the rigid electrode support assembly and housing 102. In such a configuration, a variety of different electrode support assemblies of varying shapes, sizes, and electrode configurations can be made available for physically and electrically connecting to a standard ITCS housing 102.

It is noted that the electrodes and the lead assembly 106 can be configured to assume a variety of shapes. For example, the lead assembly 106 can have a wedge or chevron shape, and the subcutaneous electrode 104 can comprise a number of spaced electrodes, such as an array or band of electrodes. Moreover, two or more subcutaneous electrodes 104 can be mounted to multiple electrode support assemblies 106 to achieve a desired spaced relationship amongst subcutaneous electrodes 104.

An ITCS device of the present invention can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference in their respective entireties.

Depending on the configuration of a particular ITCS device, a delivery system can advantageously be used to facilitate proper placement and orientation of the ITCS device housing and subcutaneous electrode(s). According to one embodiment of such a delivery system, a long metal rod similar to conventional trocars can be used to perform small diameter blunt tissue dissection of the subdermal layers. This tool may be pre-formed straight or curved to facilitate placement of the subcutaneous electrode, or it may be flexible enough to allow the physician to shape it appropriately for a given patient. An exemplary delivery tool, aspects of which can be incorporated into an ITCS device delivery tool, is disclosed in commonly owned U.S. Pat. No. 5,300,106, which is hereby incorporated herein by reference in its entirety.

Figure 2:
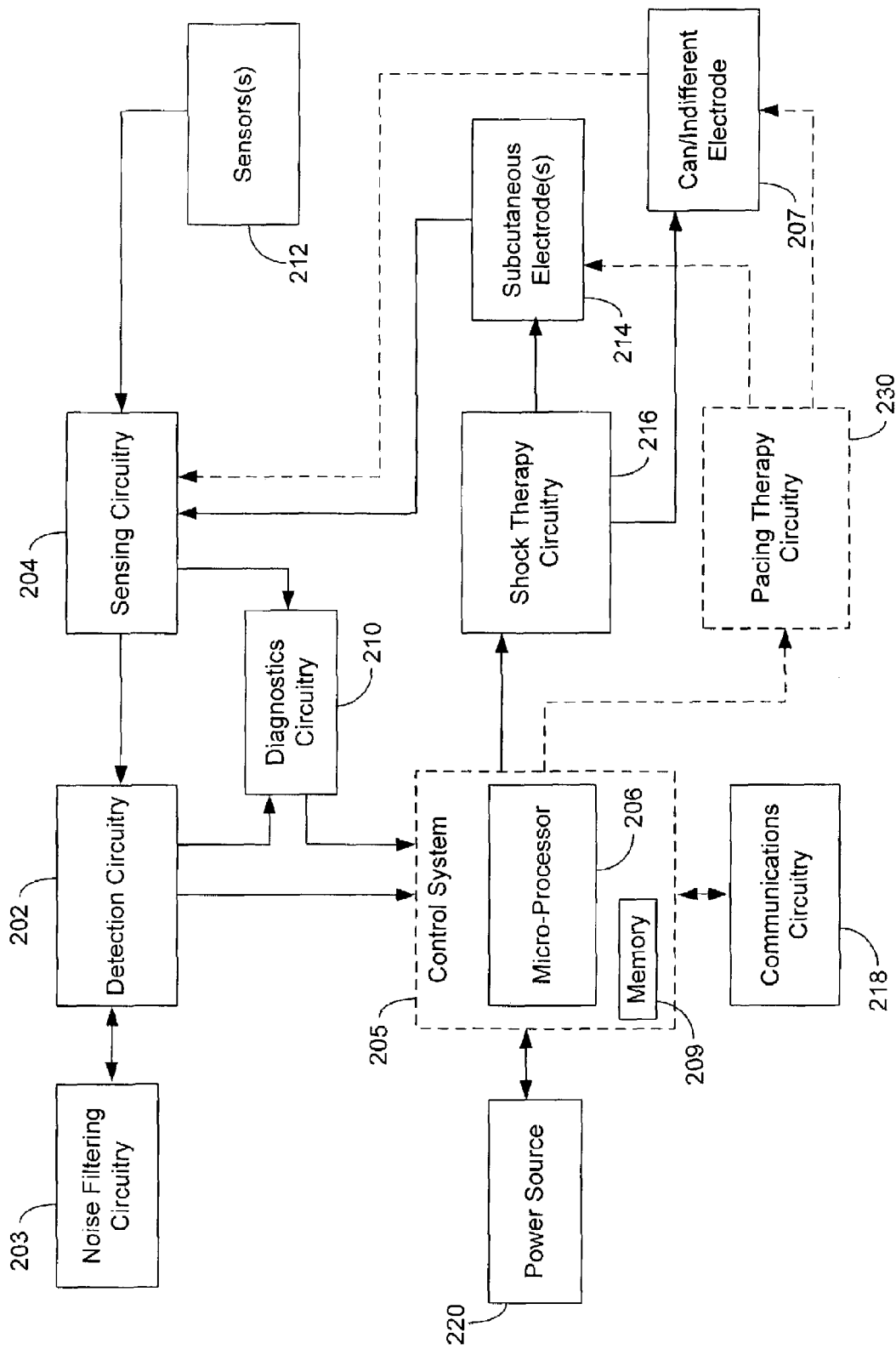
FIG. 2 is a block diagram showing various components of a transthoracic cardiac stimulation device in accordance with an embodiment of the present invention.

FIG. 2 is a block diagram depicting various components of an ITCS device in accordance with an embodiment of the present invention. According to this embodiment, the ITCS device incorporates a processor-based control system 205 which includes a micro-processor 206 coupled to appropriate memory (volatile and non-volatile) 209, it being understood that any logic-based control architecture can be used. The control system 205 is coupled to circuitry and components to sense, detect, and analyze electrical signals produced by the heart and deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high energy pulses for cardioversion or defibrillation.

Cardiac signals are sensed using the subcutaneous electrode(s) 214 and the can or indifferent electrode 207 provided on the ITCS device housing. Cardiac signals can also be sensed using only the subcutaneous electrodes 214, such as in a non-active can configuration. As such, unipolar, bipolar, or combined unipolar/bipolar electrode configurations may be employed. The sensed cardiac signals are received by sensing circuitry 204, which includes sense amplification circuitry and may also include filtering circuitry. The sensed cardiac signals processed by the sensing circuitry 204 are received by detection circuitry 202, which typically includes a signal processor and an analog-to-digital (A/D) converter.

The signal processor of the detection circuitry 202 coordinates analysis of the sensed cardiac signals and/or other sensor inputs to detect cardiac arrhythmias, such as, in particular, tachyarrhythmia. Rate based and/or morphological discrimination algorithms can be implemented by the signal processor of the detection circuitry 202 to detect and verify the presence and severity of an arrhythmic episode. Exemplary arrhythmia detection and discrimination circuitry, structures, and techniques, aspects of which can be implemented by an ITCS device of the present invention, are disclosed in commonly owned U.S. Pat. Nos. 5,301,677 and 6,438,410, which are hereby incorporated herein by reference in their respective entireties.

The detection circuitry 202 is coupled to, or otherwise incorporates, noise filtering circuitry 203. The noise filtering circuitry 203 operates to improve the signal-to-noise ratio of sensed cardiac signals by removing noise content of the sensed cardiac signals introduced from various sources. Typical types of transthoracic cardiac signal noise includes electrical noise and noise produced from skeletal muscles, for example.

The detection circuitry 202 includes an analog-to-digital converter that converts the sensed cardiac signals from analog to digital form and communicates the signals to the control system 205. Memory circuitry 209 of the control system 205 contains parameters for operating in various sensing, defibrillation, and pacing modes, and stores data indicative of cardiac signals received by the detection circuitry 202. The memory circuitry 209 can also be configured to store historical ECG and therapy data, which may be used for various purposes and transmitted to an external receiving device as needed or desired.

In certain configurations, the ITCS can include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 can incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to an embodiment that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the subcutaneous electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated embodiment, the shock therapy circuitry 216 is controlled to deliver defibrillation therapies, in contrast to an embodiment that provides for delivery of both cardioversion and defibrillation therapies. Exemplary ICD high energy delivery circuitry, structures and functionality, aspects of which can be incorporated in an ITCS device of the present invention, are disclosed in commonly owned U.S. Pat. Nos. 5,372,606; 5,411,525; 5,468,254; and 5,634,938, which are hereby incorporated herein by reference in their respective entireties.

In accordance with another embodiment, an ITCS device of the present invention incorporates a cardiac pacing capability in addition to cardioversion and/or defibrillation capabilities. As is shown in dotted lines in FIG. 2, the ITCS device can include pacing therapy circuitry 230 which is coupled to the control system 205 and the subcutaneous and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated. A pacing regimen may be modified by the control system 205.

As will be discussed in greater detail below, systems and methods of the present invention provide for delivery of cardiac pacing therapies in a manner particularly useful in a transthoracic cardiac stimulation device. Such cardiac pacing therapies can be delivered via the pacing therapy circuitry 230 as shown in FIG. 2. Alternatively, cardiac pacing therapies can be delivered via the shock therapy circuitry 216, which effectively obviates the need for separate pacemaker circuitry.

The ITCS device shown in FIG. 2 can be configured to receive signals from one or more physiologic and/or non-physiologic sensors. Depending on the type of sensor employed, signals generated by the sensors can be communicated to transducer circuitry coupled directly to the detection circuitry or indirectly via the sensing circuitry. It is noted that certain sensors can transmit sense data to the control system 205 without processing by the detection circuitry 202.

Communications circuitry 218 is coupled to the microprocessor 206 of the control system 205. The communications circuitry 218 allows the ITCS device to communicate with one or more receiving devices or systems situated external to the ITCS device. By way for example, the ITCS device can communicate with a patient-worn, portable or bed-side communication system via the communications circuitry 218. In one configuration, one or more physiologic or non-physiologic sensors (subcutaneous, cutaneous, or external of patient) can be equipped with a short-range wireless communication interface, such as an interface conforming to a known communications standard, such as Bluetooth or IEEE 802 standards. Data acquired by such sensors can be communicated to the ITCS device via the communications circuitry 218. It is noted that physiologic or non-physiologic sensors equipped with wireless transmitters or transceivers can communicate with a receiving system external of the patient.

The communications circuitry 218 can allow the ITCS device to communicate with an external programmer. In one embodiment, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the ITCS device and the programmer unit during and after implant. Using a programmer, a physician is able to set or modify various parameters used by the ITCS device. For example, a physician can set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive RF energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

Figure 3:
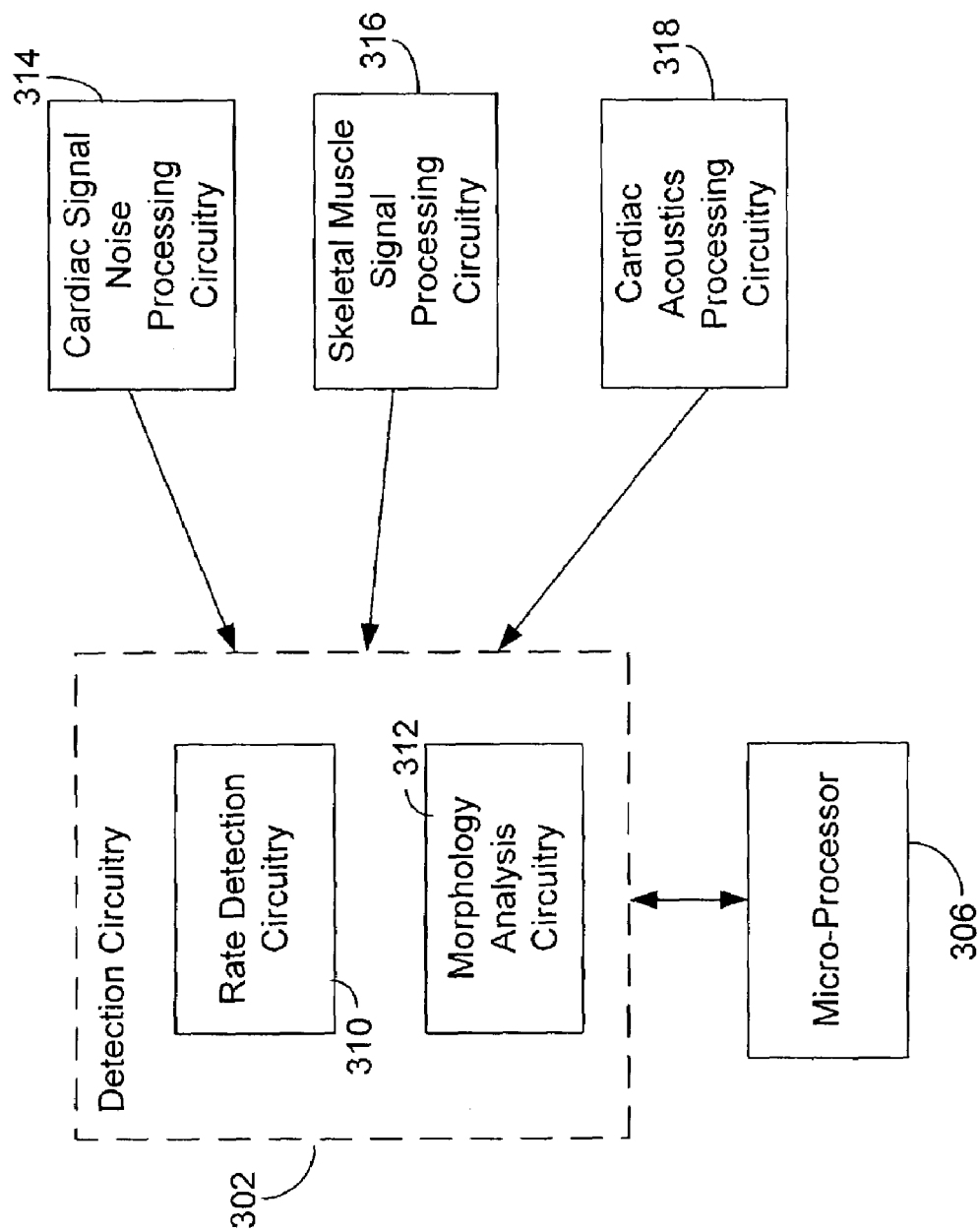
FIG. 3 is a block diagram illustrating various processing and detection components of a transthoracic cardiac stimulation device in accordance with an embodiment of the present invention.

FIG. 3 illustrates an embodiment of detection circuitry 302 of an ITCS device which includes one or both of rate detection circuitry 310 and morphological analysis circuitry 312. Detection and verification of arrhythmias can be accomplished using rate-based discrimination algorithms as known in the art implemented by the rate detection circuitry 310. Arrhythmic episode can also be detected and verified by morphology-based analysis of sensed cardiac signals as is known in the art. Tiered or parallel arrhythmia discrimination algorithms can also be implemented using both rate-based and morphologic-based approaches.

The detection circuitry 302, which is coupled to a microprocessor 306, can be configured to incorporate, or communicate with, specialized circuitry for processing sensed cardiac signals in manners particularly useful in a transthoracic cardiac stimulation device. As is shown by way of example in FIG. 3, the detection circuitry 302 can receive information from multiple physiologic and non-physiologic sensors. As illustrated, transthoracic acoustics can be monitored using an appropriate acoustic sensor. Heart sounds, for example, can be detected and processed by cardiac acoustic processing circuitry 318 for a variety of purposes. The acoustics data is transmitted to the detection circuitry 302, via a hardwire or wireless link, and used to enhance cardiac signal detection. For example, acoustics can be used to discriminate normal cardiac sinus rhythm with electrical noise from potentially lethal arrhythmias, such as ventricular tachycardia or ventricular fibrillation.

The detection circuitry 302 can also receive information from one or more sensors that monitor skeletal muscle activity. In addition to cardiac activity signals, skeletal muscle signals are readily detected by transthoracic electrodes. Such skeletal muscle signals can be used to determine the activity level of the patient. In the context of cardiac signal detection, such skeletal muscle signals are considered artifacts of the cardiac activity signal, which can be viewed as noise. Processing circuitry 316 receives signals from one or more skeletal muscle sensors, and transmits processed skeletal muscle signal data to the detection circuitry 302. This data can be used to discriminate normal cardiac sinus rhythm with electrical noise from cardiac arrhythmias.

As was previously discussed, the detection circuitry 302 is coupled to, or otherwise incorporates, noise processing circuitry 314. The noise processing circuitry 314 processes sensed cardiac signals to improve the signal-to-noise ratio of sensed cardiac signals by removing noise content of the sensed cardiac signals.

Figure 4:
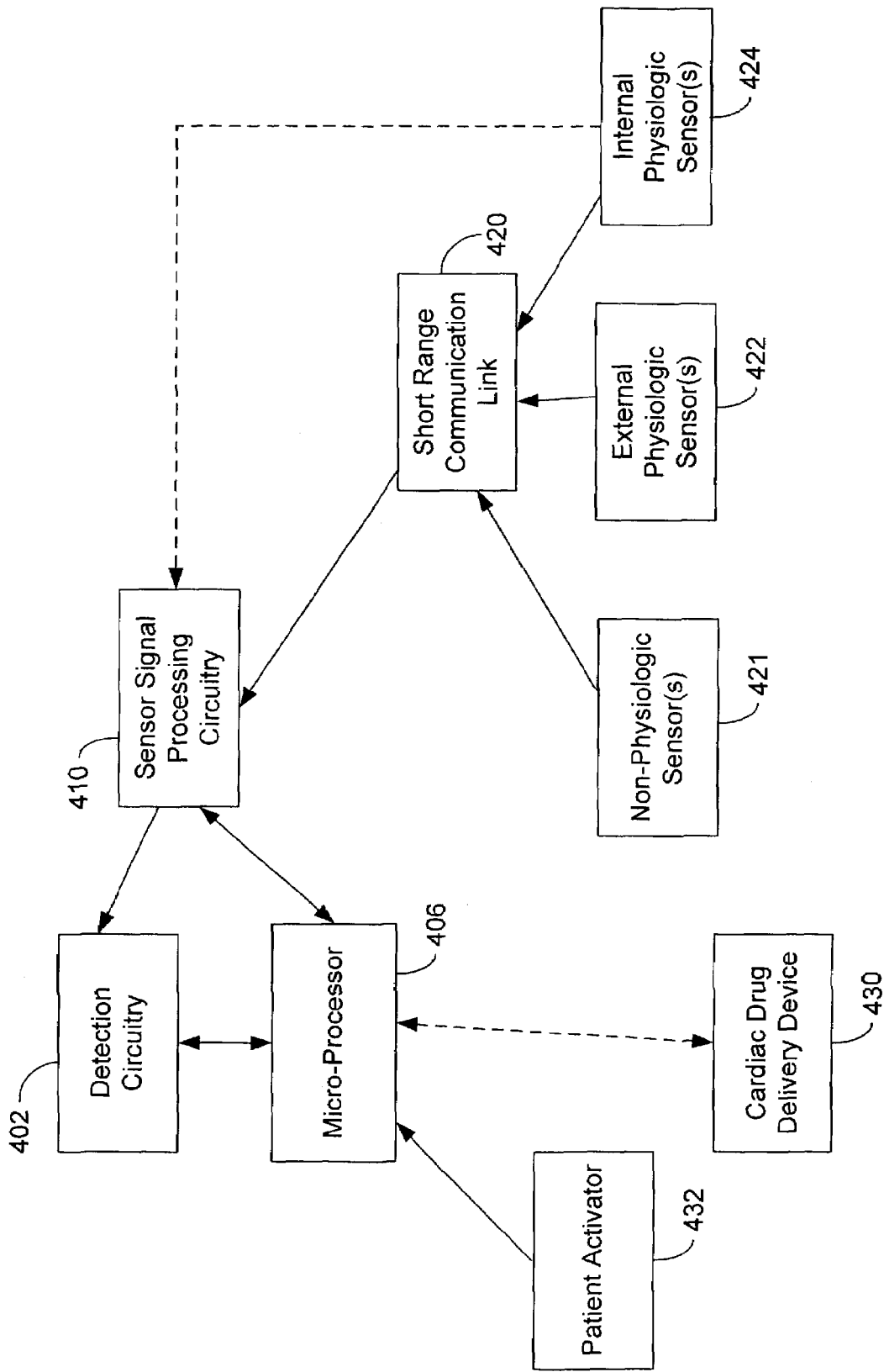
FIG. 4 is a block diagram showing various sensors, devices, and circuitry of a transthoracic cardiac stimulation device in accordance with an embodiment of the present invention.

Turning now to FIG. 4, there is illustrated a block diagram of various components of an ITCS device in accordance with an embodiment of the present invention. FIG. 4 shows a number of components that are associated with detection of various physiologic and non-physiologic parameters. As shown, the ITCS device includes a micro-processor 406, which is typically incorporated in a control system for the ITCS device, coupled to detection circuitry 402. Sensor signal processing circuitry 410 can receive sensor data from a number of different sensors.

For example, an ITCS device of the present invention can cooperate with, or otherwise incorporate, various types of non-physiologic sensors 421, external/cutaneous physiologic sensors 422, and/or internal physiologic sensors 424. Such sensors can include an acoustic sensor, an impedance sensor, an oxygen saturation sensor, and a blood pressure sensor, for example. Each of these sensors 421, 422, 424 can be communicatively coupled to the sensor signal processing circuitry 410 via a short range wireless communication link 420. Certain sensors, such as an internal physiologic sensor 424, can alternatively be communicatively coupled to the sensor signal processing circuitry 410 via a wired connection (e.g., electrical or optical connection).

A cardiac drug delivery device 430 can be employed to cooperate with an ITCS device of the present invention. For example, the cardiac drug delivery device 430 can deliver one or more anti-arrhythmic agents that have been approved for the chemical treatment of tachycardia and fibrillation. A non-exhaustive, non-limiting list of such agents includes: quinidine, procainamide, disopyramide, flecaininde, propafenone, moricizine, sotalol, amiodarone, ibutilide, and dofetilide (e.g., class III anti-arrhythmic agents). These and other drugs can be delivered prior to, during, and after delivery of cardioversion/defibrillation therapy for purposes of enhancing patient comfort, lowering defibrillation thresholds, and/or chemically treating an arrhythmic condition.

In accordance with another configuration, the ITCS device can include a non-implanted patient actuatable activator 432 that operates in cooperation with the ITCS device. The activator 432 includes a communication unit and produces an activation signal in response to a patient sensing a perceived severe arrhythmic condition. Alternatively, or in addition, the activation signal may be produced by the non-implanted activator 432 in response to the ITCS device detecting the arrhythmic condition. The ITCS device includes communication circuitry for communicating with the non-implanted activator 432.

The activator 432 can be actuated by the patient or person attending the patient to initiate cardioversion/defibrillation therapy. Typically, the ITCS device, in response to receiving an activation signal, confirms that the patient is experiencing an actual adverse cardiac condition prior to initiating appropriate therapy. The non-implanted activator 432, in communication with the ITCS device, can also generate a patient perceivable initiating signal to indicate manual or automatic commencement of a drug delivery regimen to treat the actual adverse cardiac condition.

The activator 432 can be configured to include an inhibit button that allows the patient to override the delivery of a stimulation therapy in the event that the ITCS device indicates that a potentially serious arrhythmia has been detected, but the patient determines that the detection indication is in error. Unambiguous arrhythmic episodes detected by the ITCS device are preferably subject to therapy delivery upon detection and confirmation, notwithstanding receipt of an inhibition signal from the patient activator 432.

The components, functionality, and structural configurations depicted in FIGS. 1-4 are intended to provide an understanding of various features that can be incorporated in an ITCS of the present invention. It is understood that a wide variety of ITCS configurations are contemplated, ranging from relatively sophisticated to relatively simple designs. As such, particular ITCS configurations can include particular features as described herein, while other ITCS configurations can exclude particular features described herein.

In accordance with an embodiment of the present invention, an ITCS is configured to provide both transthoracic defibrillation and pacing therapies. In certain configurations, the ITCS delivers pacing therapies using defibrillation therapy circuitry and one or more high voltage defibrillation capacitors, which eliminates the need for separate pacing therapy circuitry. In other configurations, pacing therapies of the present invention can be delivered by dedicated pacing therapy circuitry.

Particular embodiments of the present invention are directed to maintaining cardiac and vascular support by providing post-shock pacing pulses from an ITCS. Various embodiments of the present invention are directed to post-shock asystole prevention using post-shock pacing therapies. According to one approach, and in contrast to conventional bradycardia pacing modalities, normal heart rate is not maintained by the ITCS. Rather, a single pacing pulse is delivered after a predetermined interval following detection of the last R-wave or delivery of a pace pulse.

An ITCS of the present invention can be programmed to detect cardiac asystole subsequent to delivery of a defibrillation therapy and, in response, deliver a life sustaining, non-physiologic transthoracic pacing therapy to terminate the detected cardiac asystole. The pacing therapy provides for delivery of pacing pulses at a rate substantially lower than a bradycardia pacing rate. The pacing therapy can involve delivery of pacing pulses at a progressively increasing rate or at a substantially constant rate. For example, a given pacing interval can be increased by a fixed amount or a certain percentage relative to a preceding pacing interval. The pacing therapy can alternatively involve delivery of a series of pacing pulses, where the series of pacing pulses includes at least one sequence delivered at a variable rate and at least one sequence delivered at a substantially constant rate.

Cardiac pacing support according to the present invention can be utilized in an ITCS where conventional backup pacing is not available. Since there are no intracardiac electrodes available, pacing is provided subcutaneously. However, subcutaneous pacing levels are much greater then conventional intracardiac thresholds, with the potential of causing discomfort to the patient. Once the patient's heart begins to pace on its own, pacing support is terminated for that episode. It is desirable, but not required, that while pacing support is given, the patient is not fully conscious.

Pacing, in this regard, is provided only as a means to maintain patient life post shock during asystole. The maximum pacing interval is preferably short enough to maintain life, but sufficiently long enough to not enable full consciousness in the patient where pacing could be perceived as particularly painful. A suitable pacing rate typically ranges between 2 and 40 pulses per minute (ppm), with 5-20 ppm representing a typical pacing rate. The pacing electrodes may be the same as the shock electrodes or can include one or more dedicated pacing electrodes.

In one approach, energy to perform cardiac pacing support is provided by residual energy left on the defibrillation storage capacitor(s) subsequent to defibrillation therapy delivery. A maximum number of pacing pulses (e.g., 10 pulses) are deliverable post shock using the residual capacitor energy prior to charge depletion. This approach effectively eliminates the necessity of having a separate pacing circuit in the ITCS. Instead, only a simple voltage or current regulator may be utilized to maintain the proper voltage levels. Pacing pulses are thus provided through the shock delivery circuit. An exemplary set of pacing levels can include a 20 ms rectangular monophasic waveform at a maximum of 10 volts and/or 200 mA. In the event additional pacing is required, the energy storage capacitor can be quickly charged to a suitable level.

According to a further embodiment, an ITCS of the present invention can be configured to provide physiologic subcutaneous pacing. In this embodiment, a cardioversion or defibrillation therapy can be delivered in response to detecting a cardiac arrhythmia that necessitates cardioversion or defibrillation therapy. Energy for the cardioversion or defibrillation therapy is provided by a subcutaneous cardioversion/defibrillation energy storage source. A physiologic or bradycardia pacing therapy can also be delivered in response to detecting a condition necessitating pacing therapy, such as after defibrillation therapy delivery and detection of cardiac asystole. Energy for the pacing therapy delivery is provided by the defibrillation energy storage source. Alternatively, conventional pacing circuitry can be employed. The condition necessitating pacing therapy delivery can include a bradycardia condition or a tachycardia condition. According to this embodiment, the ITCS can support bradycardia and/or anti-tachycardia pacing.

An ITCS apparatus for providing subcutaneous pacing support according to an embodiment of the present invention includes a housing and energy delivery circuitry provided in the housing. The energy delivery circuitry comprises a defibrillation energy storage source according to this embodiment. First and second electrodes are respectively coupled to the energy delivery circuitry and arranged in a spaced relationship with respect to cardiac tissue and vasculature for transthoracic cardiac sensing and energy delivery. In this regard, the first and second electrodes are positioned so that these electrodes do not touch or otherwise physically contact the heart or heart vessels.

At least one of the first and second electrodes can be supported on or by the housing. Alternatively, the first and second electrodes are provided on structures not supported from the housing, and are electrically coupled with electronics within the housing via a lead(s). Detection/control circuitry is provided in the housing and coupled to the energy delivery circuitry. The detection/control circuitry detects cardiac asystole subsequent to delivery of a defibrillation therapy, and transthoracicly delivers a pacing therapy via the energy delivery circuitry to terminate the detected cardiac asystole using residual energy from the defibrillation energy storage source.

In one configuration, one of the first and second electrodes is provided on the housing, and the other electrode is provided on a medical electrical lead. In another configuration, the first and second electrodes are respectively provided on the housing, which may be a unitary housing. In a further embodiment, one of the first and second electrodes is provided on the housing, and the other electrode is provided on a support structure outwardly extending from the housing.

In yet another configuration, one or more electrodes are provided on the housing and/or a subcutaneous lead/electrode array, and a contacting electrode is connected to the housing via a lead. The contacting electrode can be an epicardial electrode (e.g., patch electrode) or an endocardial electrode. In this ITCS configuration, at least one contacting electrode and at least one non-contacting electrode can be employed.

Exemplary circuitry, structures and functionality, aspects of which can be incorporated in an ITCS device according to this embodiment, are disclosed in several of the previously incorporated patents and in commonly owned U.S. Pat. Nos. 5,314,459 and 5,531,779, which are hereby incorporated herein by reference in their respective entireties.

According to another embodiment, the detection/controller of an ITCS of the type described above detects cardiac asystole subsequent to delivery of a defibrillation therapy, and, in response, transthoracicly delivers a life sustaining, non-physiologic pacing therapy to terminate the detected cardiac asystole. In one configuration of this embodiment, defibrillation therapy and pacing therapy derive energy from a defibrillation energy storage source. In another configuration of this embodiment, pacing circuitry and defibrillation circuitry are coupled to the detection/control circuitry. Defibrillation therapy is delivered via the defibrillation circuitry and the pacing circuitry delivers the pacing therapy.

Figure 5:
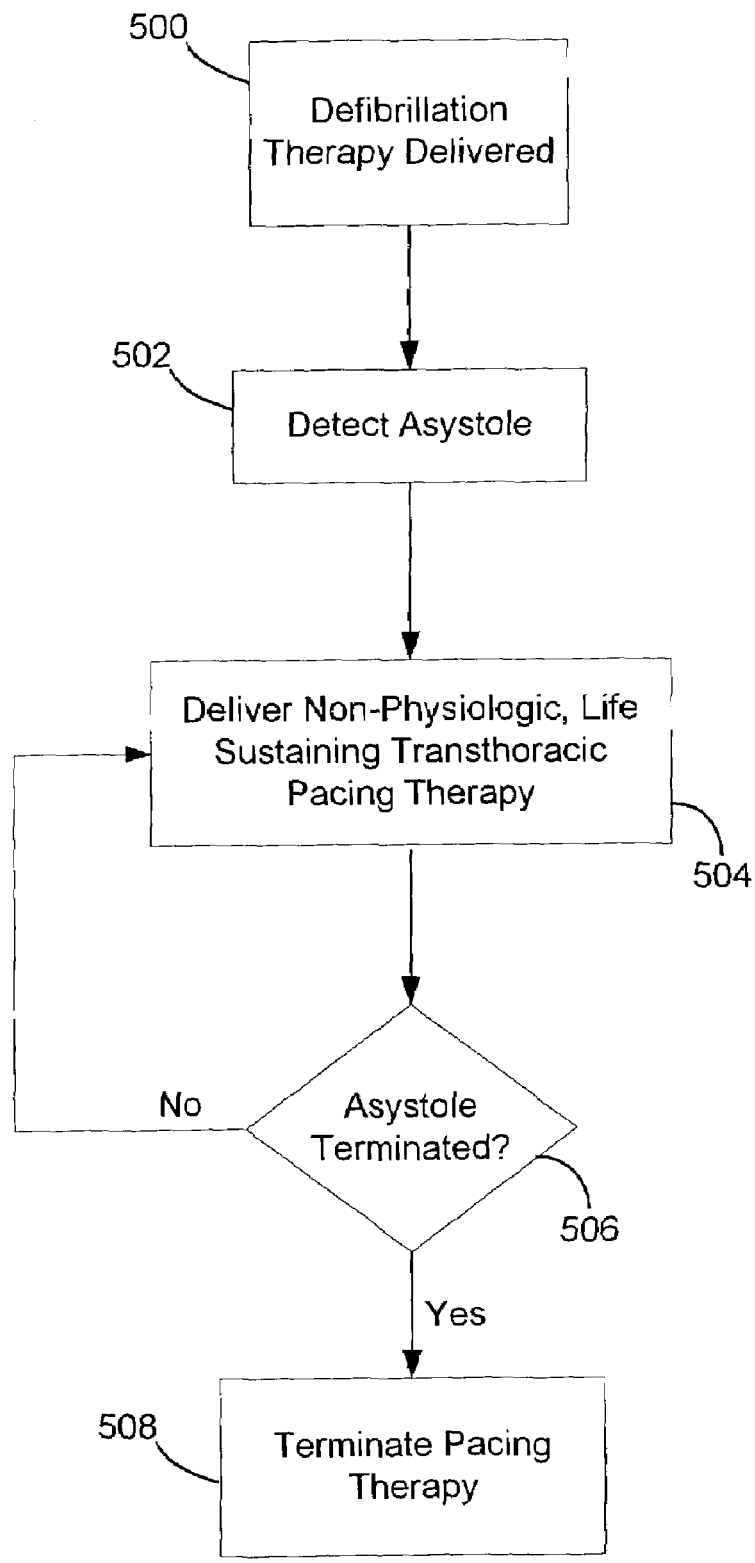
FIG. 5 is a flow diagram illustrating various processes associated with a transthoracic pacing therapy for terminating detected asystole following defibrillation therapy delivery in accordance with an embodiment of the present invention.

Turning now to FIG. 5, there is illustrated a flow diagram showing various processes associated with a transthoracic pacing therapy for terminating detected asystole following defibrillation therapy delivery in accordance with an embodiment of the present invention. According to this embodiment, defibrillation therapy is delivered 500 in response to the ITCS detecting and confirming a ventricular fibrillation episode. Alternatively, defibrillation therapy is delivered 500 in response to receipt of an activation signal from an external activator and after the ITCS detects and confirms the ventricular fibrillation episode.

Upon detecting 502 post-shock asystole of the heart, the ITCS delivers a non-physiologic, life sustaining transthoracic pacing therapy 504 in an attempt to terminate asystole. If the ITCS determines 506 that asystole has not abated, the ITCS continues to deliver non-physiologic, life sustaining transthoracic pacing therapy 504. The pacing therapy is terminated 508 in response to the ITCS detecting successful termination of asystole.

Figure 6:
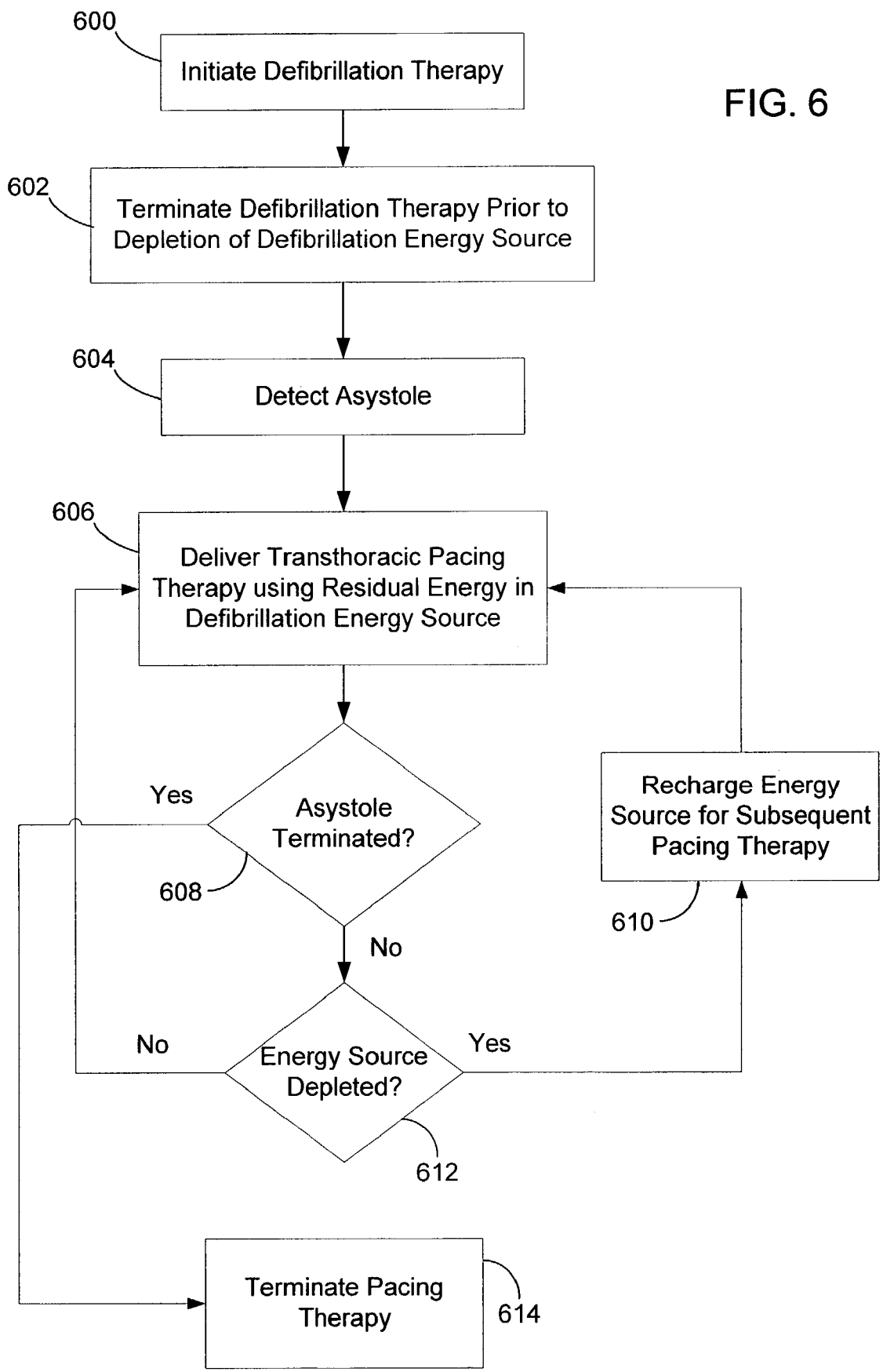
FIG. 6 is a flow diagram illustrating various processes associated with a transthoracic pacing therapy for terminating detected asystole following defibrillation therapy delivery, wherein energy for the pacing therapy is provided by a defibrillation energy storage source in accordance with an embodiment of the present invention.

FIG. 6 is a flow diagram showing various processes associated with a transthoracic pacing therapy for terminating detected asystole following defibrillation therapy delivery in accordance with another embodiment of the present invention. According to this embodiment, defibrillation therapy is initiated 600 in response to the ITCS detecting and confirming a ventricular fibrillation episode as previously described. Defibrillation therapy is terminated 602 prior to depletion of the defibrillation energy source.

The defibrillation waveform is selected to provide delivery of defibrillation energy sufficient to terminate ventricular fibrillation, while leaving sufficient energy to subsequently deliver one or more pacing pulses prior to depleting the high voltage defibrillation capacitor(s). For example, the defibrillation therapy can reduce a voltage of the defibrillation energy storage source from a first voltage level to a second voltage level, and the pacing therapy can be delivered at voltage levels equal to or less than the second voltage level. The first and second voltage levels are selected primarily to provide effective defibrillation therapy and then secondarily to provide adequate residual strength for a duration of post-shock asystole prevention pacing therapy.

Upon detecting 604 post-shock asystole, the ITCS delivers a transthoracic pacing therapy 606 using energy remaining in the defibrillation energy source in an attempt to terminate asystole. If asystole is successfully terminated 608, then transthoracic pacing therapy is terminated 614. If asystole is not terminated 608, then a check 612 is made to determine if sufficient energy remains in the defibrillation energy source to support delivery of a transthoracic pacing therapy. If depleted and asystole persists, the defibrillation energy source is recharged 610 to a depth of charge sufficient to support redelivery of the previously selected pacing therapy or another pacing therapy directed to terminating asystole. The recharging process can be repeated after delivery of a single pace pulse or a series of pulses, assuming an R-wave is not detected after delivery of a given pulse, thus indicating persistence of asystole. Depending on the duration of asystole persistence, the depth of charge can be varied from one recharge cycle to another to meet the pacing energy demands associated with a given pacing therapy. The pacing therapy is terminated 614 in response to the ITCS detecting successful termination of asystole.

Figure 7:
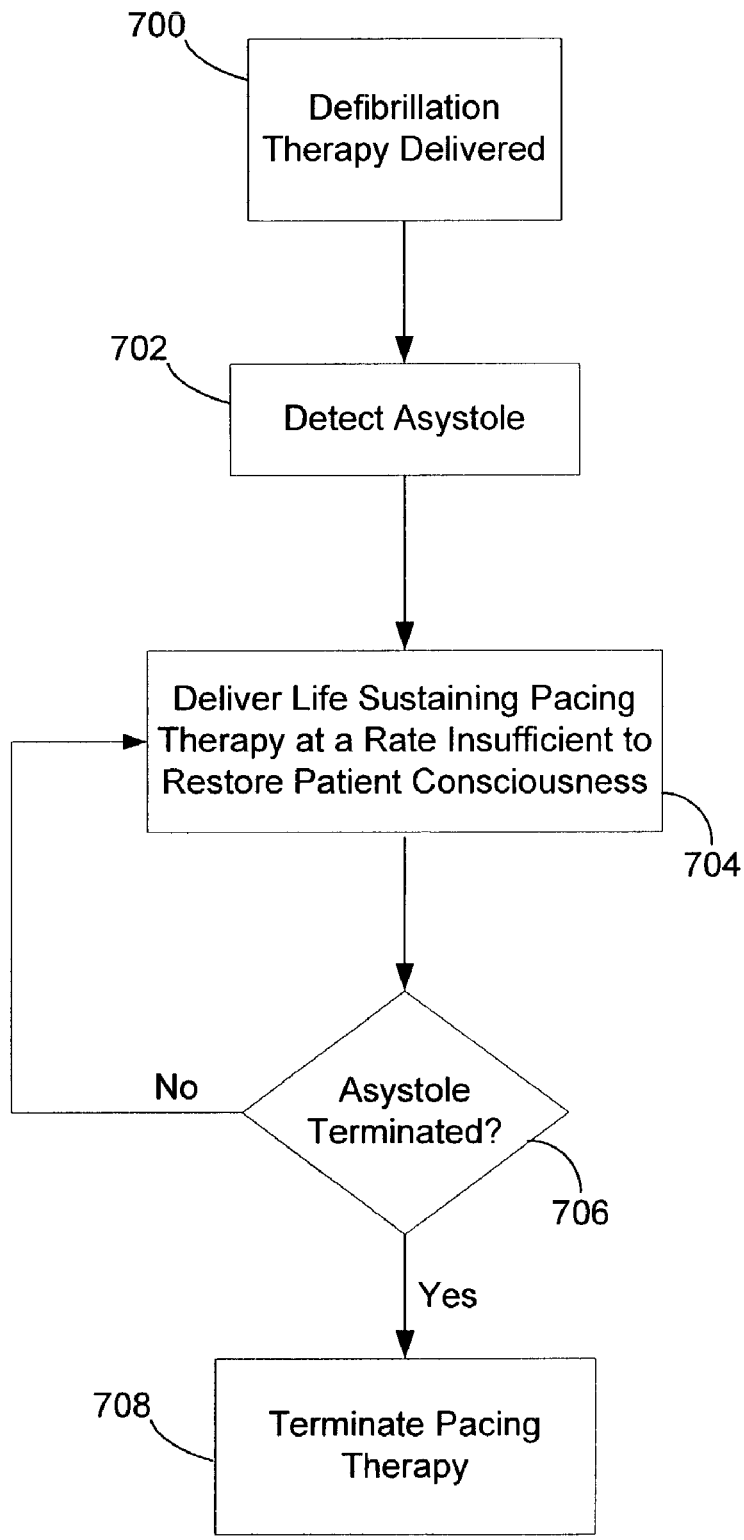
FIG. 7 is a flow diagram illustrating various processes associated with a transthoracic pacing therapy for terminating detected asystole following defibrillation therapy delivery in accordance with another embodiment of the present invention.

FIG. 7 illustrates various processes associated with another transthoracic pacing therapy for terminating detected asystole following defibrillation therapy delivery in accordance with an embodiment of the present invention. According to this embodiment, defibrillation therapy is delivered 700 in response to the ITCS detecting and confirming a ventricular fibrillation episode as previously discussed. Upon detecting 702 post-shock asystole, the ITCS delivers a pacing therapy at a rate insufficient to restore full patient consciousness 704, but sufficient to maintain life. It is assumed that the patient is unconscious or semi-conscious following a fibrillation episode and onset of asystole. Delivering post-shock pacing therapy at a rate insufficient to restore full patient consciousness is intended to maintain life while minimizing the pain or discomfort associated with subcutaneous pacing.

If the ITCS determines 706 that asystole has not terminated, the ITCS continues to deliver 704 a pacing therapy at a rate sufficient to maintain life, but insufficient to restore full patient consciousness. As discussed above, suitable pacing rates for implementing a pacing therapy according to this embodiment can range between about 2 and 40 ppm, with 5-20 ppm representing a typical pacing rate range. The pacing therapy is terminated 708 in response to the ITCS detecting successful termination of asystole.

Figure 8:
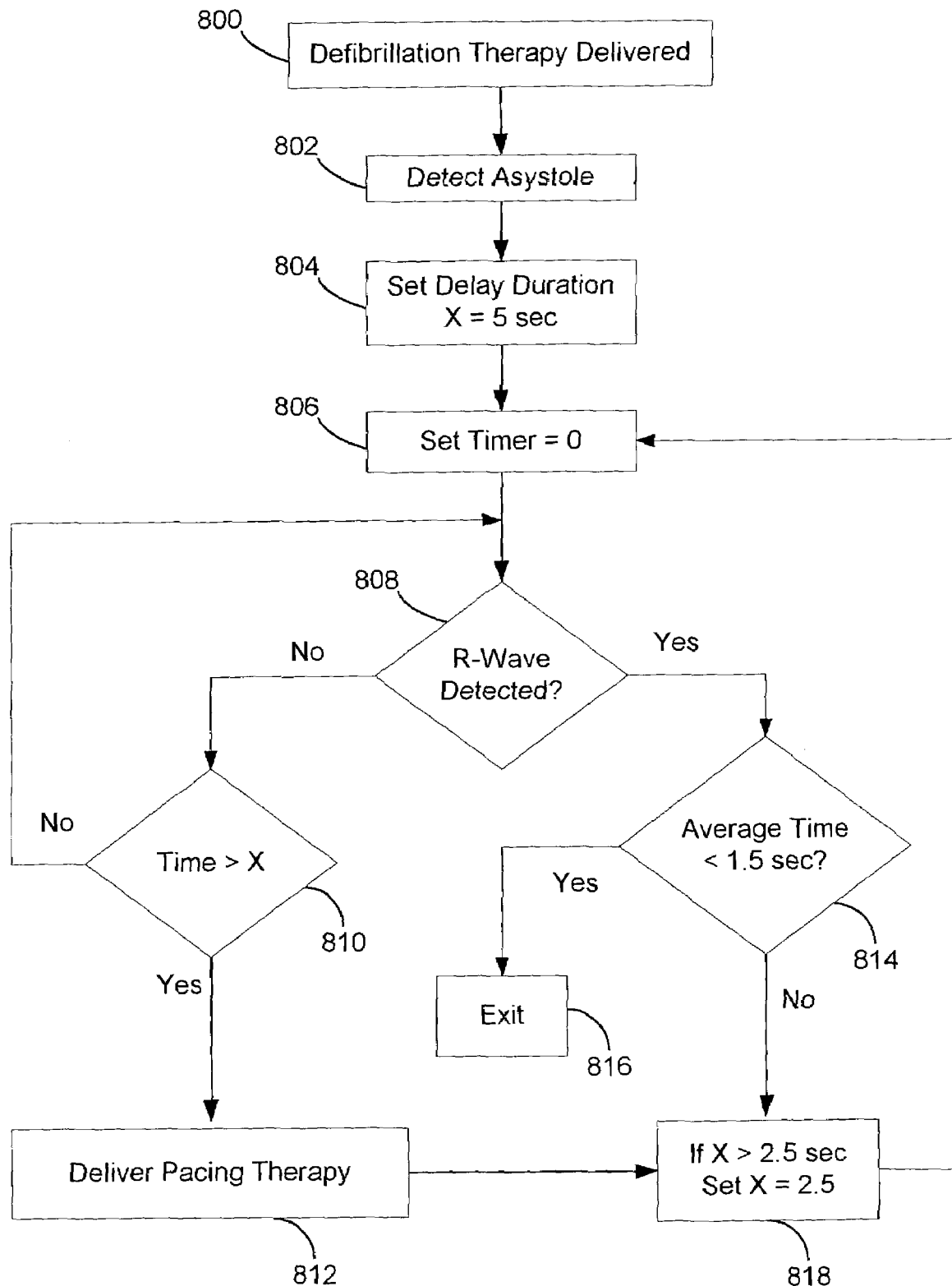
FIG. 8 is a flow diagram illustrating various processes associated with a transthoracic pacing therapy for terminating detected asystole following defibrillation therapy delivery in accordance with a further embodiment of the present invention.

An embodiment of a pacing methodology employing post-shock asystole prevention timing is depicted in FIG. 8. According to this embodiment, defibrillation therapy is delivered 800 in response to the ITCS detecting and confirming a ventricular fibrillation episode as previously discussed. Upon detecting 802 post-shock asystole, control circuitry within the ITCS initiates post-shock asystole prevention timing which controls the delivery of a pacing therapy in a manner depicted in FIG. 8.

A delay duration, X, is set 804, such as X=5 seconds. The delay duration is representative of the amount of time that post-shock asystole prevention pacing is delayed after detection of asystole. This delay period is selected to allow for the spontaneous termination of asystole for a particular patient or patient population, which would obviate the need for post-shock asystole prevention pacing. In the illustrative embodiment of FIG. 8, the delay duration, X, is set to 5 seconds, it being understood that the delay duration, X, can range from about 2-3 seconds up to about 30 seconds.

A timer is initialized 806 by setting the timer to 0. The ITCS senses for cardiac activity, in the form of R-wave detection. If an R-wave is detected 808, and the average time between 2 or more successive detected R-waves is determined 814 to be less than 1.5 seconds, then the ITCS confirms that asystole has been terminated and the pacing therapy routine is exited 816. If the average time between detected R-waves is not less than 1.5 seconds 814, then the delay duration, X, is set to X=2.5 seconds if X is greater than 2.5 seconds 818, otherwise the current value of the delay duration, X, is retained. The timer is reinitialized to 0, and processing continues at process 806.

If an R-wave is not detected 808 and the timer has exceeded 810 the delay duration, X, then pacing therapy is delivered 812. The delay duration, X, is set to X=2.5 seconds if X is greater than 2.5 seconds 818, otherwise the current value of the delay duration, X, is retained. This reduction in the delay duration, X, effectively shortens the time to the next pacing pulse, assuming an R-wave is not detected. Although process 818 can initially reduce the delay duration, X, by 50%, it is understood that the delay duration, X, can be shortened by greater or less than 50%, such as between 30% and 80% of a preceding delay duration. Moreover, the delay duration, X, can be progressively reduced until a predetermined minimum duration is reached, such as by reducing the delay duration, X, by a fixed percentage or fixed amount of time until the predetermined minimum duration is reached.

Figure 9:
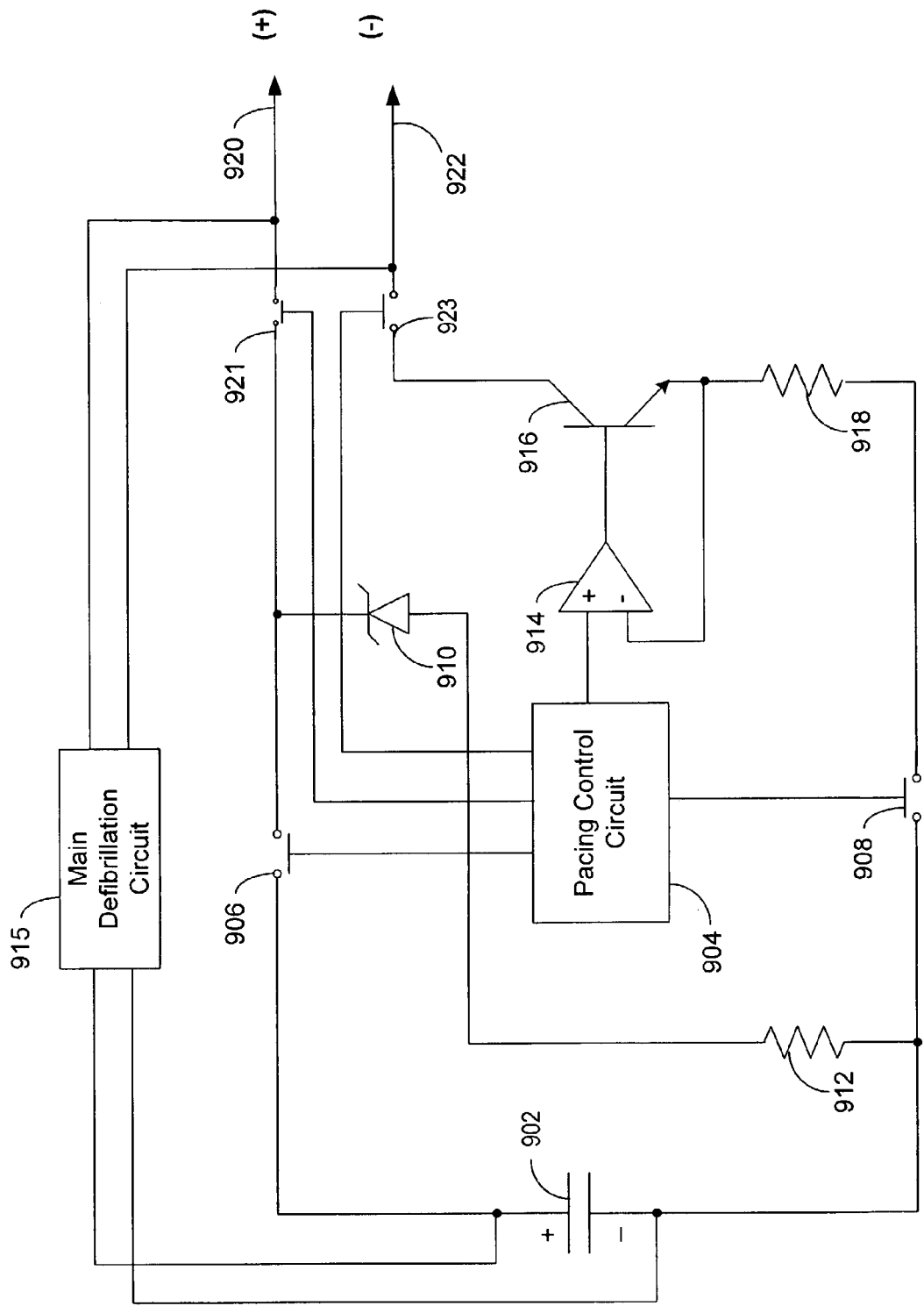
FIG. 9 is a schematic of circuitry for delivering a transthoracic pacing therapy for terminating detected asystole following defibrillation therapy delivery in accordance with an embodiment of the present invention.

FIG. 9 is a simplified schematic of circuitry for delivering post-shock asystole prevention pacing in accordance with an embodiment of the present invention. The circuitry shown in FIG. 9 is coupled to, or otherwise incorporated within, the defibrillation circuit of the ITCS, details of which are not shown for purposes of simplicity. The circuitry shown in FIG. 9 includes a defibrillation energy source 902, which is coupled to the main energy unit (e.g., battery, not shown) of the ITCS. The defibrillation energy source 902 can include one or more high voltage capacitors of a type typically used in defibrillation devices.

The main defibrillation circuit 915 is shown coupled to high voltage terminals 920 and 922 and the defibrillation energy source 902. The pacing control circuit 904 is shown coupled to switches 906 and 908, which are respectively coupled to the defibrillation energy source 902 and high voltage terminals 920 and 922 via switches 921 and 923, respectively (switch 908 coupled to terminal 922 via pacing current control circuitry). Operation of the main defibrillation circuit 915 and pacing control circuit 904 is controlled by a control system (not shown) of the ITCS to selectively enable and disable primary defibrillation circuitry, associated with shock therapy delivery, and asystole prevention circuitry, associated with pacing therapy delivery.

When in a defibrillation therapy delivery mode, switches 906, 908, 921 and 923 are opened, which disables the asystole prevention circuitry, enabling the main defibrillation circuitry 915 to delivery normal defibrillation therapy via terminals 920, 922 without interfering with the asystole prevention circuitry. When in a post-shock asystole prevention pacing mode, switches 906, 908, 921, and 923 are closed by the pacing control circuit 904, which enables the post-shock asystole prevention pacing circuitry.

A desired pacing voltage is maintained across terminals 920, 922 via a Zener diode 910 (e.g., 200 V nominal or less) and a resistor 912. The pacing control circuit 904 can control the current of the pace pulses via transistor 916 and control amplifier 914, such as between about 10 mA and about 500 mA. In one approach, the pacing pulses preferably have a peak current no greater than about 200 mA.

It is noted that the main defibrillation circuitry 915 typically includes an H-bridge circuit (not shown) for switching the polarity of the defibrillation waveform during therapy delivery. Those skilled in the art will appreciate that other control circuit configurations can be implemented to provide post-shock asystole prevention pacing via a defibrillation energy source in accordance with the principles of the present invention.

Figure 10:
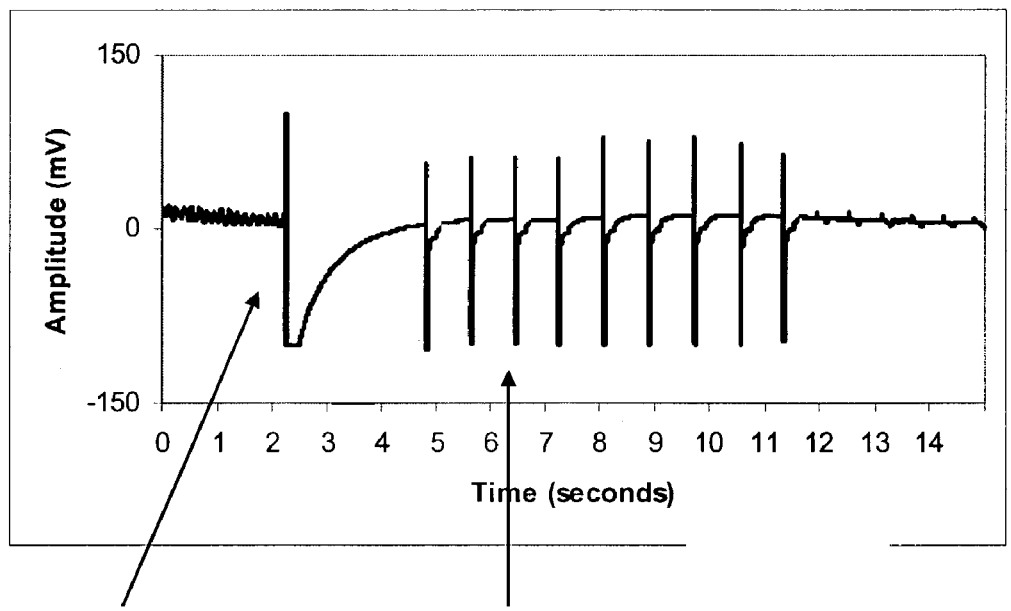
FIG. 10 is an illustration of a typical bradycardia pacing waveform sequence associated with a conventional post-shock pacing mode.

FIG. 10 is a waveform sequence illustrating typical bradycardia pacing (e.g., VVI) subsequent to defibrillation therapy. Post-shock pacing according to a conventional approach involves pacing the heart at a physiologic rate, such as at 70 ppm. The waveform shown in FIG. 11, in contrast to that of FIG. 10, illustrates post-shock asystole prevention pacing according to an embodiment of the present invention. One skilled in the art will readily appreciate that the pacing waveform shown in FIG. 11 represents a non-physiologic pacing therapy that delivers pacing pulses at a rate substantially below a conventional bradycardia pacing rate, but at a rate sufficient to sustain life.

Figure 11:
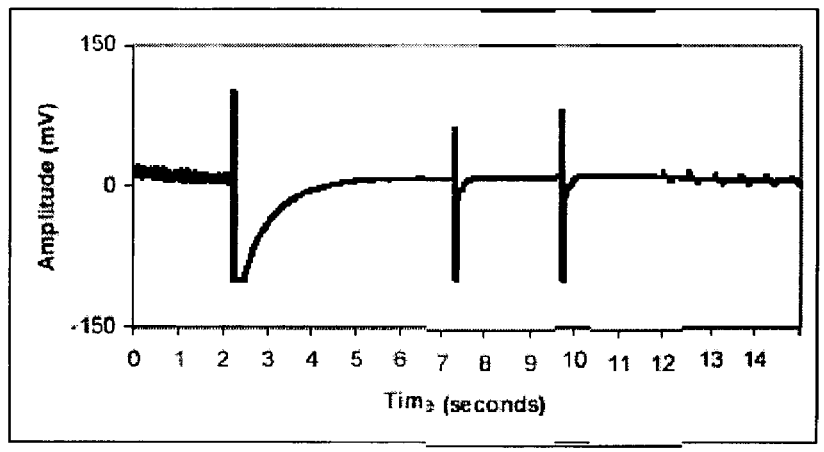
FIG. 11 is a waveform sequence representative of a transthoracic pacing therapy for terminating detected asystole following defibrillation therapy delivery in accordance with an embodiment of the present invention.
Figure 11:
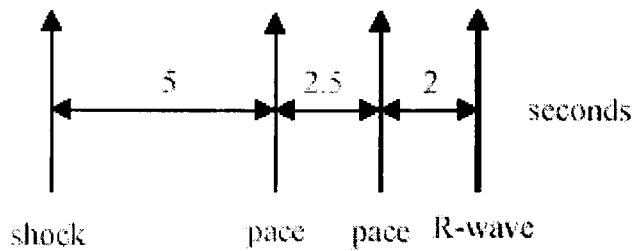

FIG. 11 further illustrates one approach to post-shock asystole prevention pacing in which the pacing rate progressively increases to a predetermined maximum pacing rate at predetermined increments. By way of example, and as is shown in FIG. 11, the first pace pulse following detection of post-shock asystole is delayed by a predetermined initial delay period, such as 5 seconds. Upon detecting non-termination of asystole after delivering the first pace pulse, a second delay period (e.g., 2.5 seconds) is initiated which is shorter in duration than the initial delay period. A second pace pulse is delivered after expiration of the second delay period.

Upon detecting non-termination of asystole after delivering the second pace pulse, a third delay period (e.g., 2.0 seconds) is initiated which is shorter in duration than the second delay period. If necessary, another pace pulse would be delivered after expiration of the third delay period. This progression in pacing interval decrease continues until a predetermined minimum pacing interval (maximum pacing rate) is reached, such as a pacing interval of 2.0 seconds. In the illustrative example shown in FIG. 11, an R-wave is detected prior to the end of the third delay period, thereby inhibiting the third pace pulse. Subsequent R-waves occur at an average interval that exceeds the minimum pacing interval, and pacing is terminated.

It will be appreciated that other pacing therapies can be implemented in accordance with a post-shock asystole prevention pacing methodology of the present invention. For example, pacing pulses can be delivered at a rate varying between about 2 and about 40 pulses per minute. According to one approach, a first pace pulse can be delivered after an initial delay of about 5 to 30 seconds subsequent to detection of the cardiac asystole, and subsequent pace pulses can be delivered at an increased pacing rate, such as at a progressively increasing rate. For example, a first pace pulse can be delivered after a first duration subsequent to detection of the cardiac asystole, and a second pace pulse can be delivered after a second duration subsequent to the first pace pulse, where the second duration can range between about one-third and about three-fourths of the first duration.

A series of pacing pulses can alternatively be delivered at a substantially constant rate. A post-shock asystole prevention pacing therapy can also involve delivering a series of pacing pulses, where the series of pacing pulses includes at least one sequence delivered at a variable rate and at least one sequence delivered at a substantially constant rate.

Figure 12:
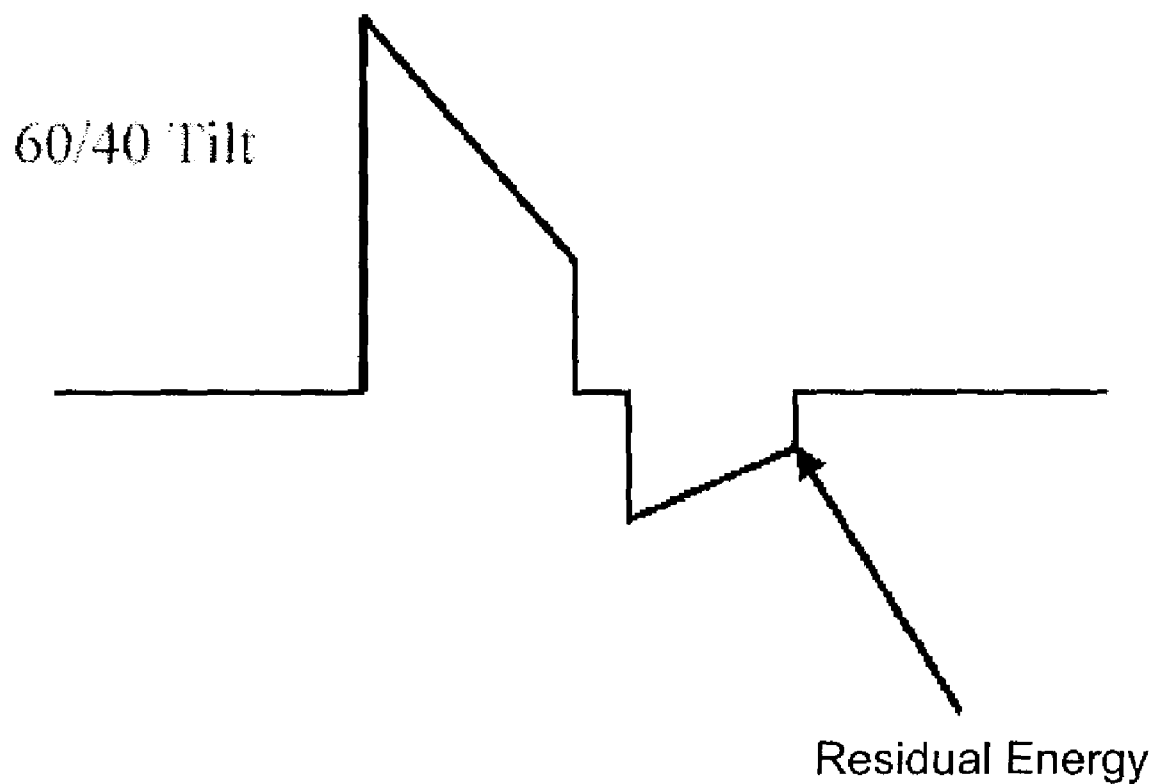
FIG. 12 is a defibrillation waveform that provides for residual energy sufficient to support a transthoracic pacing therapy for terminating detected asystole following defibrillation therapy delivery in accordance with an embodiment of the present invention.

FIG. 12 illustrates a defibrillation waveform of a type suitable for implementing a post-shock asystole prevention pacing therapy of the present invention. In general, the defibrillation waveform is selected to provide delivery of defibrillation energy sufficient to terminate ventricular fibrillation, while leaving sufficient energy to subsequently deliver one or more pacing pulses prior to depleting the remaining defibrillation energy in the storage source. In particular, the overall tilt of the shock waveform can be selected to provide for a residual charge on the defibrillation capacitor(s) sufficient to deliver one or more pacing pulses prior to capacitor depletion.

The shock waveform shown in FIG. 12, for example, has a so-called 60/40 tilt, which results in an overall tilt of 76% given the characteristics of the particular capacitor (e.g., 150 µF capacitor) of the defibrillation circuitry. In general, an overall tilt of 70%-80% is typically sufficient to provide enough residual energy to support post-shock asystole prevention pacing therapy. In other words, the residual energy to be used for post-shock asystole prevention pacing therapy is typically 10% or less of the total energy of the capacitor(s) when fully charged for defibrillation therapy. However, the overall tilt of the defibrillation waveform can range between about 0% and 90%. It is noted that the defibrillation waveform can be a monophasic, a biphasic, or a multiphasic (e.g., triphasic) waveform of a known type. For example, the defibrillation waveform can be a biphasic, truncated exponential waveform.

Figure 13:
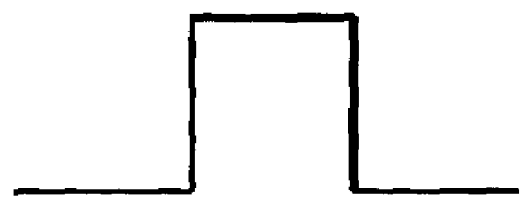
FIG. 13 is a pacing pulse waveform associated with a transthoracic pacing therapy for terminating detected asystole following defibrillation therapy delivery in accordance with an embodiment of the present invention.

In FIG. 12, about 5.8% of the fully charged capacitor energy is remaining after defibrillation therapy delivery. Assuming that the overall tilt of the shock waveform in FIG. 12 is 76%, a shock that delivers 50 joules will result in 2.9 joules of residual energy to support post-shock asystole prevention pacing therapy. If a 200 mA rectangular pacing pulse having a 20 ms pulse width is delivered post-shock (assuming 50 ohms transthoracic impedance), as is shown in FIG. 13, the energy associated with ten of such pacing pulses is 0.4 joules. It is noted that the pacing pulse width can be varied between about 10 ms and 30 ms. It is readily appreciated that preserving a relatively small amount of post-shock energy provides the opportunity to deliver a substantial number of pacing pulses for purposes of terminating post-shock cardiac asystole without adversely affecting the efficacy of the defibrillation therapy.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of providing subcutaneous cardiac stimulation, comprising:
    detecting from a subcutaneous, non-intrathoracic vector, cardiac asystole subsequent to delivery of a defibrillation therapy, energy for the defibrillation therapy provided by a subcutaneous, non-intrathoracic defibrillation energy storage source; and
    delivering, from the same or different subcutaneous, non-intrathoracic vector, a pacing therapy to terminate the detected cardiac asystole using residual energy from the defibrillation energy storage source.

2. The method of claim 1, wherein the residual energy usable for the pacing therapy delivery represents less than about 10% of energy initially stored in the defibrillation storage source prior to defibrillation therapy delivery.

3. The method of claim 1, wherein the residual energy usable for the pacing therapy is sufficient to transthoracicly deliver a plurality of pacing pulses.

4. The method of claim 3, further comprising detecting for cardiac asystole termination following delivery of each of the pacing pulses, and terminating subcutaneous pacing support in response to detecting cardiac asystole termination.

5. The method of claim 1, wherein the defibrillation therapy reduces a voltage of the defibrillation energy storage source from a first voltage level to a second voltage level, and the pacing therapy is effected at a voltage level equal to or less than the second voltage level.

6. The method of claim 1, wherein delivering the pacing therapy comprises using the residual energy until either the pacing therapy terminates the detected cardiac asystole or the defibrillation energy storage source is depleted of the residual energy.

7. The method of claim 6, further comprising recharging the defibrillation energy storage source in response to depletion of the residual energy.

8. The method of claim 7, further comprising re-delivering the pacing therapy or an alternative transthoracic pacing therapy in response to recharging the defibrillation energy storage source, wherein re-delivering the pacing therapy or the alternative transthoracic pacing therapy is initiated after recharging the defibrillation energy storage source to a level less than that associated with the defibrillation therapy.

9. The method of claim 1, wherein the residual energy used for delivering the pacing therapy is sufficient to transthoracicly deliver a single pacing pulse.

10. The method of claim 9, further comprising recharging, following delivery of the single pacing pulse, the defibrillation energy storage source to a recharge level less than a level associated with defibrillation therapy delivery.

11. The method of claim 10, wherein the recharge level of the defibrillation energy storage source is sufficient to support delivery of a subsequent single pacing pulse.

12. The method of claim 10, wherein the recharge level of the defibrillation energy storage source is sufficient to support delivery of a plurality of pacing pulses.

13. The method of claim 1, wherein delivering the pacing therapy comprises delivering one or more pacing pulses each having a peak current no greater than about 500 mA.

14. The method of claim 1, wherein delivering the pacing therapy comprises delivering one or more pacing pulses each having a pulse width of about 20 ms.

15. The method of claim 1, wherein delivering the pacing therapy comprises delivering one or more pacing pulses each having a pulse width varying between about 10 ms and about 30 ms.

16. The method of claim 1, wherein a defibrillation waveform generated from the defibrillation therapy has an overall tilt of about 0% to about 90%.

17. The method of claim 1, wherein a defibrillation waveform generated from the defibrillation therapy has an overall tilt of about 40% to about 90%.

18. The method of claim 1, wherein a defibrillation waveform generated from the defibrillation therapy comprises a monophasic waveform.

19. The method of claim 1, wherein a defibrillation waveform generated from the defibrillation therapy comprises a biphasic waveform.

20. The method of claim 1, wherein a defibrillation waveform generated from the defibrillation therapy comprises a multiphasic waveform.

21. The method of claim 1, wherein the pacing therapy is delivered using defibrillation electrodes.

22. The method of claim 1, wherein the pacing therapy is delivered using pacing electrodes.

23. A method of providing subcutaneous cardiac stimulation, comprising:
    detecting, from within a patient, cardiac asystole subsequent to delivery of a defibrillation therapy; and
    transthoracicly delivering, from within the patient, a non-physiologic, life sustaining pacing therapy at a rate substantially lower than a bradycardia pacing rate to terminate the detected cardiac asystole.

24. The method of claim 23, wherein delivering the pacing therapy comprises delivering a first pace pulse about 5 to 20 seconds subsequent to detection of the cardiac asystole.

25. The method of claim 23, wherein delivering the pacing therapy comprises delivering a first pace pulse about 20 to 30 seconds subsequent to detection of the cardiac asystole.

26. The method of claim 23, wherein delivering the pacing therapy comprises delivering a plurality of pacing pulses at a progressively increasing rate.

27. The method of claim 23, wherein delivering the pacing therapy comprises delivering a plurality of pacing pulses at a substantially constant rate.

28. The method of claim 23, wherein delivering the pacing therapy comprises delivering a series of pacing pulses, the series of pacing pulses comprising at least one sequence delivered at a variable rate and at least one sequence delivered at a substantially constant rate.

29. The method of claim 23, wherein delivering the pacing therapy comprises:
delivering a first pace pulse after a first duration subsequent to detection of the cardiac asystole; and
delivering a second pace pulse after a second duration subsequent to the first pace pulse, the second duration being about one-third to about three-fourths of the first duration.

30. The method of claim 23, wherein delivering the pacing therapy comprises:
delivering a first pace pulse after a first duration subsequent to detection of the cardiac asystole; and
delivering a second pace pulse after a second duration subsequent to the first pace pulse, the second duration being shorter than the first duration by a fixed amount.

31. The method of claim 30, wherein the fixed amount ranges between about 5 seconds and about 15 seconds.

32. The method of claim 23, wherein delivering the pacing therapy comprises delivering pacing pulses at a rate varying between about 2 and about 40 pulses per minute.

33. The method of claim 23, wherein the defibrillation therapy and the pacing therapy derive energy from a defibrillation energy storage source.

34. The method of claim 23, wherein the defibrillation therapy derives energy from a defibrillation energy storage source, and the pacing therapy derives energy from a pacing circuitry power source.

35. A method of providing subcutaneous cardiac stimulation, comprising:
detecting, from with a patient, cardiac asystole subsequent to delivery of a defibrillation therapy; and
transthoracicly delivering, from within the patient, a life sustaining pacing therapy at a rate insufficient to restore full patient consciousness to terminate the detected cardiac asystole.

36. The method of claim 35, wherein delivering the pacing therapy comprises delivering pacing pulses at a rate substantially lower than a bradycardia pacing rate.

37. The method of claim 35, wherein delivering the pacing therapy comprises delivering pacing pulses at a rate varying between about 2 and about 40 pulses per minute.

38. The method of claim 35, wherein delivering the pacing therapy comprises delivering a first pace pulse about 5 to 20 seconds subsequent to detection of the cardiac asystole.

39. The method of claim 35, wherein delivering the pacing therapy comprises delivering a first pace pulse about 20 to 30 seconds subsequent to detection of the cardiac asystole.

40. The method of claim 35, wherein delivering the pacing therapy comprises delivering a plurality of pacing pulses at a progressively increasing rate.

41. The method of claim 35, wherein delivering the pacing therapy comprises delivering a plurality of pacing pulses at a substantially constant rate.

42. The method of claim 35, wherein delivering the pacing therapy comprises delivering a series of pacing pulses, the series of pacing pulses comprising at least one sequence delivered at a variable rate and at least one sequence delivered at a substantially constant rate.

43. A method of providing subcutaneous cardiac stimulation, comprising:
delivering, from a subcutaneous, non-intrathoracic vector, a pacing therapy in response to detecting a condition necessitating pacing therapy delivery, energy for the pacing therapy delivery provided by a subcutaneous, non-intrathoracic cardioversion/defibrillation energy storage source; and
delivering, from the same or a different subcutaneous, non-intrathoracic vector, a cardioversion or defibrillation therapy in response to detecting a cardiac arrhythmia necessitating the cardioversion or defibrillation therapy, energy for the cardioversion or defibrillation therapy provided by the subcutaneous, non-intrathoracic cardioversion/defibrillation energy storage source.

44. The method of claim 43, wherein the condition necessitating pacing therapy comprises a bradycardia condition.

45. The method of claim 43, wherein the condition necessitating pacing therapy comprises a tachycardia condition.

46. An apparatus for providing subcutaneous cardiac stimulation, comprising:
an implantable housing;
energy delivery circuitry provided in the housing, the energy delivery circuitry comprising a defibrillation energy storage source;
first and second electrodes respectively coupled to the energy delivery circuitry and arranged in a spaced relationship with respect to cardiac tissue and vasculature for subcutaneous, non-intrathoracic cardiac sensing and energy delivery; and detection|control circuitry provided in the housing and coupled to the energy delivery circuitry, the detection/control circuitry detecting cardiac asystole subsequent to delivery of a defibrillation therapy and transthoracicly delivering a pacing therapy via the energy delivery circuitry to terminate the detected cardiac asystole using residual energy from the defibrillation energy storage source, wherein the residual energy used for delivering the pacing therapy is sufficient to transthoracicly deliver a single pacing pulse, and the detection/control circuitry, following delivery of the single pacing pulse, initiates recharging of the defibrillation energy storage source to a recharge level less than a level associated with defibrillation therapy delivery.

47. The apparatus of claim 46, wherein the residual energy usable for the pacing therapy delivery represents less than about 10% of energy initially stored in the defibrillation storage source prior to defibrillation therapy delivery.

48. The apparatus of claim 46, wherein the residual energy usable for the pacing therapy is sufficient to transthoracicly deliver a plurality of pacing pulses.

49. The apparatus of claim 46, wherein the detection/control circuitry comprises a detector for detecting cardiac asystole termination following delivery of each of a plurality of pacing pulses, the detection/control circuitry terminating subcutaneous pacing support in response to the detector detecting cardiac asystole termination.

50. The apparatus of claim 46, wherein the energy delivery circuitry delivers the pacing therapy using the residual energy until either the detection/control circuitry detects cardiac asystole termination or the defibrillation energy storage source is depleted of the residual energy.

51. The apparatus of claim 50, wherein the detection/control circuitry initiates recharging of the defibrillation energy storage source in response to depletion of the residual energy.

52. The apparatus of claim 46, wherein the detection/control circuitry initiates re-delivery of the pacing therapy or an alternative transthoracic pacing therapy in response to recharging of the defibrillation energy storage source, wherein re-delivery of the pacing therapy or the alternative transthoracic pacing therapy is initiated after recharging the defibrillation energy storage source to a level less than that associated with the defibrillation therapy.

53. The apparatus of claim 46, wherein the pacing therapy delivered by the energy delivery circuitry comprises one or more pacing pulses each having a peak current no greater than about 500 mA.

54. The apparatus of claim 46, wherein the pacing therapy delivered by the energy delivery circuitry comprises one or more pacing pulses each having a pulse width of between about 10 ms and 30 ms.

55. The apparatus of claim 46, wherein a defibrillation waveform generated by the energy delivery circuitry has an overall tilt of about 0% to about 90%.

56. The apparatus of claim 46, wherein the energy delivery circuitry delivers pacing pulses at a rate varying between about 2 and about 40 pulses per minute.

57. The apparatus of claim 46, wherein the energy delivery circuitry delivers a first pace pulse after a first duration subsequent to detection of the cardiac asystole, and delivers a second pace pulse after a second duration subsequent to the first pace pulse, the second duration being about one-third to about three-fourths of the first duration.

58. The apparatus of claim 46, wherein the energy delivery circuitry delivers a first pace pulse after a first duration subsequent to detection of the cardiac asystole, and delivers a second pace pulse after a second duration subsequent to the first pace pulse, the second duration being shorter than the first duration by a fixed amount.

59. The apparatus of claim 58, wherein the fixed amount ranges between about 5 seconds and about 15 seconds.

60. The apparatus of claim 46, wherein a defibrillation waveform generated by the energy delivery circuitry comprises a monophasic waveform.

61. The apparatus of claim 46, wherein a defibrillation waveform generated by the energy delivery circuitry comprises a biphasic waveform.

62. The apparatus of claim 46, wherein a defibrillation waveform generated by the energy delivery circuitry comprises a multiphasic waveform.

63. The apparatus of claim 46, wherein the first electrode is provided on the housing, and the second electrode is electrically and physically coupled to the housing via a lead.

64. The apparatus of claim 46, wherein the housing defines a unitary structure, and each of the first and second electrodes is respectively provided on the housing.

65. The apparatus of claim 64, wherein the housing comprises an arcuate or angled portion, and the first and second electrodes are respectively positioned proximate opposing ends of the housing.

66. The apparatus of claim 46, wherein one or both of the first and second electrodes is provided on a support structure outwardly extending from the housing.

67. The apparatus of claim 66, further comprising a header block disposed between the support structure and the housing, the header block comprising an electrical connection arrangement for coupling electrical terminals of the housing with conductors respectively coupled to the first and second electrodes.

68. The apparatus of claim 66, wherein all or a portion of the support structure comprises a shape adjustable arrangement, whereby an orientation between the first and second electrodes is alterable in response to manual manipulation of the shape adjustable arrangement.

69. The apparatus of claim 46, wherein a longitudinal axis defined between the first and second electrodes passes through at least some of the cardiac tissue.

70. An apparatus for providing subcutaneous cardiac stimulation, comprising:
 an implantable housing;
 energy delivery circuitry provided in the housing;
 first and second electrodes respectively coupled to the energy delivery circuitry and arranged in a spaced relationship with respect to cardiac tissue and vasculature for subcutaneous, non-intrathoracic cardiac sensing and energy delivery, one or both of the first and second electrodes provided on a support structure outwardly extending from the housing, all or a portion of the support structure comprises a shape adjustable arrangement, whereby an orientation between the first and second electrodes is alterable in response to manual manipulation of the shape adjustable arrangement; and
 a detection/control circuitry provided in the housing and coupled to the energy delivery circuitry, the detection/control circuitry detecting cardiac asystole subsequent to delivery of a defibrillation therapy and transthoracicly delivering a non-physiologic, life sustaining pacing therapy to terminate the detected cardiac asystole.

71. The apparatus of claim 70, wherein the defibrillation therapy and the pacing therapy derive energy from a defibrillation energy storage source of the energy delivery circuitry.

72. The apparatus of claim 70, further comprising pacing circuitry coupled to the detection/control circuitry, wherein the energy delivery circuitry delivers the defibrillation therapy and the pacing circuitry delivers the pacing therapy.

73. The apparatus of claim 70, wherein the energy delivery circuitry delivers a pacing therapy at a rate insufficient to restore full patient consciousness.

74. The apparatus of claim 70, wherein the energy delivery circuitry delivers a pacing therapy at a rate substantially lower than a bradycardia pacing rate.

75. The apparatus of claim 70, wherein the energy delivery circuitry delivers pacing pulses at a rate varying between about 2 and about 40 pulses per minute.

76. The apparatus of claim 70, wherein the energy delivery circuitry delivers one or more pacing pulses each having a pulse width of between about 10 ms and 30 ms.

77. The apparatus of claim 70, wherein the energy delivery circuitry delivers a first pace pulse about 5 to 30 seconds subsequent to detection of the cardiac asystole.

78. The apparatus of claim 70, wherein the energy delivery circuitry delivers a plurality of pacing pulses at a progressively increasing rate.

79. The apparatus of claim 70, wherein the energy delivery circuitry delivers a plurality of pacing pulses at a substantially constant rate.

80. The apparatus of claim 70, wherein the first electrode is provided on the housing, and the second electrode is electrically and physically coupled to the housing via a lead.

81. The apparatus of claim 70, wherein the housing defines a unitary structure, and each of the first and second electrodes is respectively provided on the housing.

82. The apparatus of claim 81, wherein the housing comprises an arcuate or angled portion, and the first and second electrodes are respectively positioned proximate opposing ends of the housing.

83. The apparatus of claim 70, further comprising a header block disposed between the support structure and the housing, the header block comprising an electrical connection arrangement for coupling electrical terminals of the housing with conductors coupled to respective first and second electrodes.

* * * * *